(12) United States Patent
Quintero et al.

(10) Patent No.: US 11,490,885 B2
(45) Date of Patent: Nov. 8, 2022

(54) METHODS OF USING TISSUE ANCHORS HAVING BI-DIRECTIONAL ARRAYS OF BARBED PINS FOR JOINING TOGETHER PARALLEL TISSUE LAYERS

(71) Applicant: Ethicon, Inc., Somerville, NJ (US)

(72) Inventors: Julian Quintero, Flemington, NJ (US); Leo Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 252 days.

(21) Appl. No.: 16/906,133

(22) Filed: Jun. 19, 2020

(65) Prior Publication Data

US 2020/0315606 A1 Oct. 8, 2020

Related U.S. Application Data

(62) Division of application No. 15/669,085, filed on Aug. 4, 2017, now Pat. No. 10,716,558.

(51) Int. Cl.
*A61B 17/04* (2006.01)
*A61B 17/064* (2006.01)
(Continued)

(52) U.S. Cl.
CPC ...... *A61B 17/0401* (2013.01); *A61B 17/0469* (2013.01); *A61B 17/0487* (2013.01);
(Continued)

(58) Field of Classification Search
CPC . A61B 17/064; A61B 17/068; A61B 17/0643; A61B 17/0401; A61B 17/11;
(Continued)

(56) References Cited

U.S. PATENT DOCUMENTS 3,981,051 A 9/1976 Brumlik
4,060,089 A 11/1977 Noiles
(Continued)

FOREIGN PATENT DOCUMENTS

AU 625522 7/1992
WO 0156477 8/2001
(Continued)

OTHER PUBLICATIONS

International Search Report issued in related International Application No. PCT/US2018/041353, dated Oct. 17, 2018, 6 pages.

*Primary Examiner* — Majid Jamialahmadi

(57) ABSTRACT

A method of joining together two tissue layers includes positioning a tissue anchor over a first tissue layer. The tissue anchor includes a plate having top and bottom surfaces, an array of first pins projecting from the bottom surface of the plate that oppose the first tissue layer, and an array of second pins projecting from the top surface of the plate that face away from the first tissue layer. A second tissue layer is placed over the first tissue layer and the tissue anchor so that the second pins oppose the second tissue layer. The second tissue layer is pressed onto the tissue anchor and toward the first tissue layer so that the first pins advance into the first tissue layer and the second pins advance into the second tissue layer for joining together the first and second tissue layers. The plate has second pin apertures and the second pins are free to slide and move independently of one another within the second pin apertures.

20 Claims, 16 Drawing Sheets

(51) Int. Cl.
  *A61B 17/068* (2006.01)
  *A61B 17/00* (2006.01)
  *A61B 90/00* (2016.01)

(52) U.S. Cl.
  CPC .......... *A61B 17/064* (2013.01); *A61B 17/068* (2013.01); *A61B 2017/00004* (2013.01); *A61B 2017/00579* (2013.01); *A61B 2017/00792* (2013.01); *A61B 2017/00796* (2013.01); *A61B 2017/00893* (2013.01); *A61B 2017/0641* (2013.01); *A61B 2017/0647* (2013.01); *A61B 2090/0801* (2016.02)

(58) Field of Classification Search
  CPC .................. A61B 17/115; A61B 17/08; A61B 2017/1103; A61B 2017/1107; A61B 2017/1132; A61B 2017/00579; A61B 2017/0641; A61B 2017/081
  See application file for complete search history.

(56) References Cited

U.S. PATENT DOCUMENTS

| | | |
|---|---|---|
| 4,610,250 A | 9/1986 | Green |
| 5,234,448 A | 8/1993 | Wholey et al. |
| 5,336,233 A * | 8/1994 | Chen ................. A61B 17/11 606/154 |
| 5,569,272 A | 10/1996 | Reed et al. |
| 6,036,704 A | 3/2000 | Yoon |
| 6,270,517 B1 | 8/2001 | Brotz |
| 6,620,178 B1 | 9/2003 | Brotz |
| 6,645,226 B1 | 11/2003 | Jacobus et al. |
| 6,991,643 B2 | 1/2006 | Saadat |
| 8,303,609 B2 | 11/2012 | Lentz et al. |
| 8,337,537 B2 | 12/2012 | Pelo et al. |
| 8,585,721 B2 | 11/2013 | Kirsch |
| 8,888,778 B2 | 11/2014 | Roman |
| 8,945,156 B2 | 2/2015 | Kubiak et al. |
| 2005/0234510 A1 | 10/2005 | Zamierowski |
| 2006/0235469 A1 | 10/2006 | Viola |
| 2007/0162030 A1 | 7/2007 | Aranyi et al. |
| 2010/0114301 A1 | 5/2010 | Heaton, II et al. |
| 2011/0098732 A1 | 4/2011 | Jacobs |
| 2012/0010635 A1 | 1/2012 | Yeretsian |
| 2012/0109188 A1 | 5/2012 | Viola |
| 2013/0172915 A1 | 7/2013 | Thomas et al. |
| 2015/0272724 A1 | 10/2015 | Griffin et al. |

FOREIGN PATENT DOCUMENTS

| | | |
|---|---|---|
| WO | 02096299 | 12/2002 |
| WO | 2007134215 | 11/2007 |
| WO | 2011112888 | 9/2011 |
| WO | 2012103205 | 8/2012 |
| WO | 2014078431 | 5/2014 |
| WO | 2014146000 | 9/2014 |

* cited by examiner

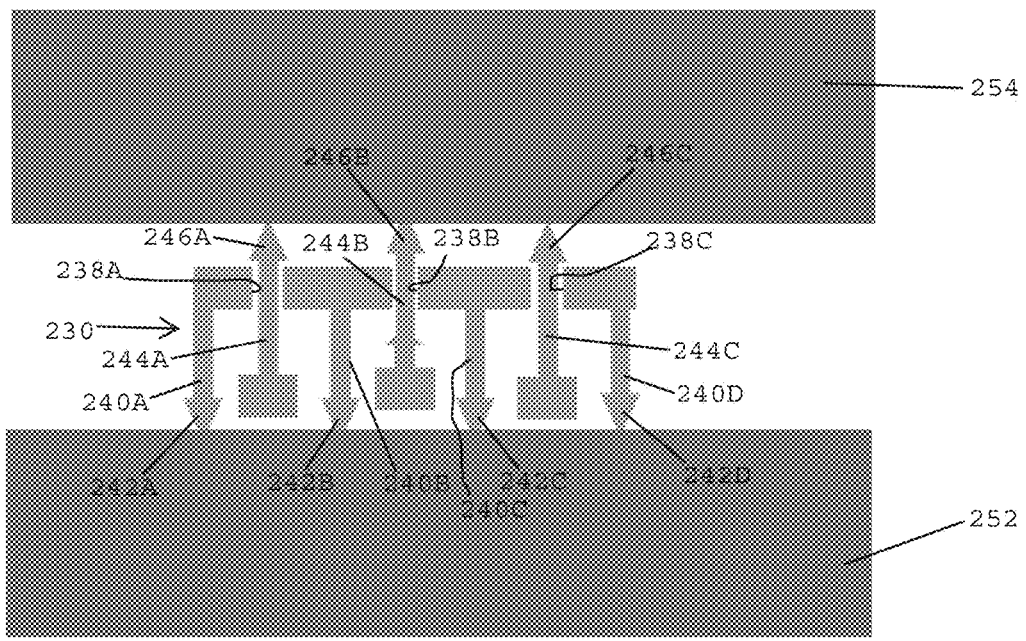
FIG. 2B
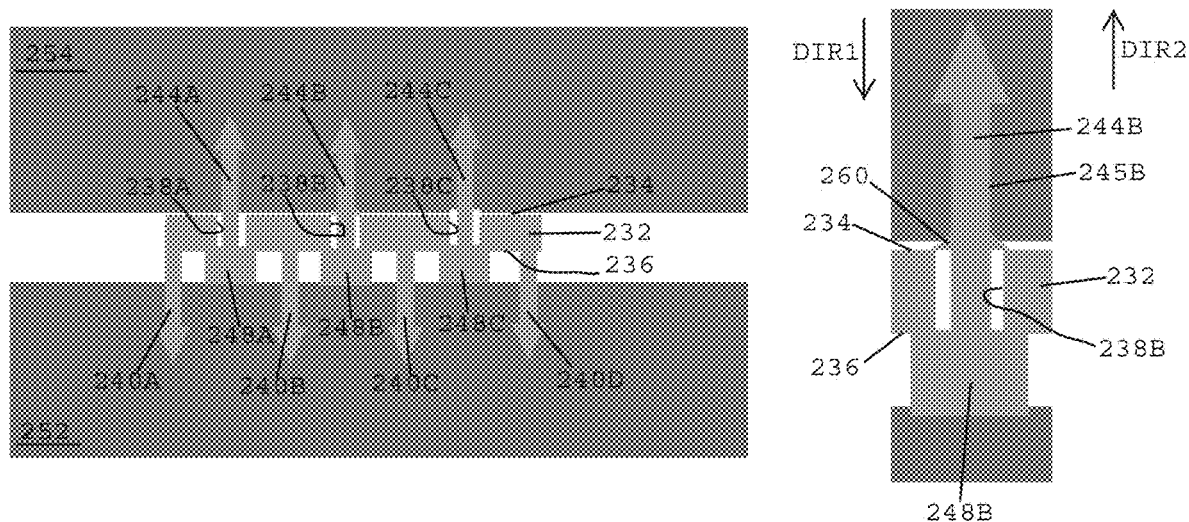
FIG. 2C
FIG. 2C-1

METHODS OF USING TISSUE ANCHORS HAVING BI-DIRECTIONAL ARRAYS OF BARBED PINS FOR JOINING TOGETHER PARALLEL TISSUE LAYERS

CROSS-REFERENCE TO RELATED APPLICATIONS

The present patent application is a divisional application of U.S. patent application Ser. No. 15/669,085, filed on Aug. 4, 2017, now allowed, the disclosure of which is hereby incorporated by reference herein.

BACKGROUND OF THE INVENTION

Field of the Invention

The present patent application is generally related to surgical procedures, and is more specifically related to surgical procedures used for joining tissue layers and closing wounds.

Description of the Related Art

The requirement to join parallel tissue layers together, which is often confronted during abdominoplasties, mastectomies, and tissue flap attachment procedures, is very challenging for surgeons and medical personnel.

An abdominoplasty is a surgical procedure that involves the removal of excess skin and fat from the middle and lower abdomen in order to tighten the muscle and fascia of the abdominal wall. The surgery is usually sought by patients with loose or sagging tissues after pregnancy or major weight loss.

A complete abdominoplasty typically involves the following steps: 1) making an incision from hip to hip just above the pubic area; 2) making another incision to free the navel from the surrounding skin; 3) detaching the skin from the abdominal wall to reveal the muscles and fascia that is required to be tightened; 4) tightening the muscle fascia wall with sutures; 4) using liposuction to refine the transition zones of the abdominal area; 5) applying a dressing and/or a compression garment; and 6) draining any excess fluid from the surgical site. https://en.wikipedia.org/wiki/Abdominoplasty.

A common post-operative complication after an abdominoplasty procedure is the collection of fluid under the skin after the drains have been removed. Typically, surgeons attempt to aspirate the fluid using a needle.

A mastectomy is a medical procedure that is frequently used to treat breast cancer and remove cancerous tissues. In the alternative, some patients may choose to have a wide local excision, also known as a lumpectomy, an operation in which a small volume of breast tissue containing the tumor and a surrounding margin of healthy tissue is removed to conserve the breast. Both mastectomy and lumpectomy are referred to as "local therapies" for breast cancer, targeting the area of the tumor, as opposed to systemic therapies, such as chemotherapy, hormonal therapy, or immunotherapy, https://en.wikipedia.org/wiki/Mastectomy.

A tissue flap attachment procedure is used in plastic and reconstructive surgery where any type of tissue is lifted from a donor site and moved to a recipient site with an intact blood supply. Tissue flap attachment procedures are used to fill defects such as a wound resulting from injury or surgery when the remaining tissue is unable to support a graft, or to rebuild more complex anatomic structures such as a breast or jaw. https://en.wikipedia.org/wiki/Flap_(surgery).

At present, there are not effective and cost efficient methodologies for joining parallel tissue layers together at the conclusion of abdominoplasties, mastectomies, and tissue flap attachment procedures. Some surgeons use compression garments to hold the parallel tissue layers together. Other surgeons use sutures, which involves a lengthy procedure that has not been proven to be effective.

Thus, in there is a continuing need for improved systems, devices, and methods for rejoining parallel tissue layers to reduce the length of surgeries, minimize complications, achieve proper healing, reduce seroma formation, eliminate the need for compression garments, and reduce the need for drainage tubes.

SUMMARY OF THE INVENTION

In one embodiment, tissue anchors are utilized for joining together two parallel layers of tissue. In one embodiment, the tissue anchors may include absorbable, bi-directional barbed or hooked pins. In one embodiment, the barbed or hooked pins may be cut, molded and/or printed. In one embodiment, in order to more effectively grip different types of tissue, a tissue anchor may have a first barb on a first pin that has a different design than a second barb on a second pin. In one embodiment, a pin may have more than one barb provided at a distal end of the pin or along the length of the pin. In one embodiment, a tissue stopper ring or similar device may be utilized to allow surgical personnel to control the depth of pin penetration into tissue.

In one embodiment, multiple tissue anchors may be placed at various locations on a first tissue layer (e.g., the rectus muscle layer). Once the tissue anchors are in place on the first tissue layer, a second tissue layer may be positioned atop the first tissue layer in order to prepare the two tissue layers for being rejoined. In one embodiment, pressure may be applied to the second tissue layer to allow the barbs on the bi-directional pins to engage e.g., hook) onto both tissue layers for achieving approximation. In one embodiment, the tissue anchors may be deployed manually. In one embodiment, the tissue anchors may be deployed using a medical device, such as a tacking device. In one embodiment, the tissue anchors are absorbable so that they eventually degrade and are absorbed by a patient's body. In one embodiment, one or more tissue anchors may be used in combination with a tissue glue or adhesive for joining parallel tissue layers together.

In one embodiment, a tissue anchor for joining tissue layers desirably includes a plate having a top surface and a bottom surface. In one embodiment, the tissue anchor may include an array of first pins coupled with the plate. In one embodiment, each of the first pins preferably includes an elongated shaft having a lower end with a first barb facing away from the bottom surface of the plate. In one embodiment, the plate desirably has an array of second pin apertures that are offset from the first pins, whereby each second pin aperture has a diameter and extends from the top surface to the bottom surface of the plate.

In one embodiment, the tissue anchor desirably has an array of second pins extending through the second pin apertures, whereby each second pin has an elongated shaft having an upper end including a second barb facing away from the top surface of the plate and a lower end including a stop that is located below the bottom surface of the plate. In one embodiment, the elongated shafts of the second pins have outer diameters that are smaller than the diameters of the second pin apertures formed in the plate for allowing the elongated shafts of the second pins to slide within the second pin apertures. In one embodiment, the second barbs and the stops of the second pins have outer diameters that are larger than the diameters of the second pin apertures for maintaining the second pins within the second pin apertures.

In one embodiment, the first barbs on the first pins preferably face in a first direction and the second barbs on the second pins preferably face in a second direction that is opposite the first direction.

In one embodiment, the second pins are configured to slide along axes that are perpendicular to the top and bottom surfaces of the plate. In one embodiment, at least one of the second pins includes a locking element provided between the upper and lower ends of the elongated shaft of one or more of the second pins. In one embodiment, the locking element provides a tactile or audible feedback to indicate that the second pin has been locked in place. In one embodiment, the locking element is closer to the stop at the lower end of the elongated shaft than the barb at the upper end of the elongated shaft.

In one embodiment, the locking element projects outwardly from the elongated shaft and is adapted to engage the plate for allowing the second barb to move a predetermined distance away from the top surface of the plate while preventing the second barb from moving back toward the top surface of the plate after the second barb has moved the predetermined distance away from the top surface of the plate.

In one embodiment, the first pins project away from the plate along axes that are perpendicular to the bottom surface of the plate. In one embodiment, the first pins have proximal ends that are affixed to the plate.

In one embodiment, one or more of the first or second pins may extend along an axis that is not perpendicular to the surfaces of the plate. In one embodiment, at least one of the second pins extends along an axis that is not perpendicular to the bottom surface of the plate.

In one embodiment, the first and second pins extend along respective axes that are parallel to one another.

In one embodiment, the elongated shafts of the second pins have a length of about 2-15 mm and a diameter of about 0.5-5 mm. In one embodiment, the second barbs of the second pins have outer diameters of about 0.3-0.5 mm. In one embodiment, the stops of the second pins have outer diameters of about 0.5-5 mm.

In one embodiment, the tissue anchor is preferably made of absorbable or non-absorbable materials.

In one embodiment, the plate of the tissue anchor may have an array of first pin apertures that are offset from the second pin apertures. In one embodiment, each of the first pin apertures has a diameter, and each first pin aperture preferably extends from the top surface to the bottom surface of the plate.

In one embodiment, the array of first pins extend through the first pin apertures. In one embodiment, each first pin preferably has an elongated shaft having a lower end including the first barb facing away from the bottom surface of the plate and an upper end including a stop that is located above the top surface of the plate. In one embodiment, the elongated shafts of the first pins have outer diameters that are smaller than the diameters of the first pin apertures for allowing the elongated shafts of the first pins to slide within the first pin apertures. In one embodiment, the first barbs and the stops of the first pins have outer diameters that are larger than the diameters of the first pin apertures for limiting sliding movement of the first pins.

In one embodiment, a kit includes a plurality of tissue anchors as disclosed herein. In one embodiment, the plurality of tissue anchors are deployable between opposing surfaces of two tissue layers for joining the tissue layers together. In one embodiment, the tissue anchors in a kit may have different sizes and/or configurations. For example, in one embodiment, a first tissue anchor may have barbs that are larger than barbs found on other tissue anchors in the kit. In another embodiment, the pins on a tissue anchor may be longer or shorter than the pins on other tissue anchors in the kit. The kit may have different types of tissue anchors that may be used for different areas of a body (e.g., for use in fattier tissue; for use in denser tissue).

In one embodiment, a method of using a tissue anchor for joining first and second tissue layers may include positioning the tissue anchor over a first tissue layer so that the first barbs of the first pins are in contact with the first tissue layer and the second barbs of the second pins face away from the first tissue layer. In one embodiment, the method may include, after the positioning step, placing a second tissue layer over the first tissue layer and the tissue anchor positioned over the first tissue layer so that the second barbs of the second pins oppose the second tissue layer. In one embodiment, the method includes after the placing step, pressing the second tissue layer onto the tissue anchor and toward the first tissue layer so that the first pins advance into the first tissue layer and the second pins advance into the second tissue layer for joining the first and second tissue layers together.

In one embodiment, during the positioning step, a plurality of the tissue anchors may be positioned over the first tissue layer so that the first barbs of the first pins are in contact with the first tissue layer and the second barbs of the second pins face away from the first tissue layer.

In one embodiment, during the placing step, the second tissue layer is placed over the plurality of tissue anchors so that the second barbs of the second pins oppose the second tissue layer.

In one embodiment, after the placing step, the second tissue layer is pressed onto the plurality of the tissue anchors and toward the first tissue layer so that the first pins advance into the first tissue layer and the second pins advance into the second tissue layer for joining the first and second tissue layers together.

In one embodiment, a tissue anchor for joining tissue layers may include a plate having a top surface and a bottom surface, and an array of first pins coupled with the plate, whereby each first pin includes an elongated shaft having a lower end including a first barb facing away from the bottom surface of the plate. In one embodiment, the tissue anchor desirably includes an array of second pins coupled with the plate, whereby each second pin includes an elongated shaft including an upper end including a second barb facing away from the top surface of the plate. In one embodiment, the first and second pins are offset from one another. In one embodiment, the first and second pins extend away from one another on opposite sides of the plate.

In one embodiment, the first barbs have a first dimension and the second barbs have a second dimension that is different than the first dimension. In one embodiment, one or more of the first barbs has a first dimension and one or more of the second barbs has a second dimension that is different than the first dimension of the one or more first barbs.

In one embodiment, the elongated shafts of the first pins have a first length and the elongated shafts of the second pins have a second length that is different than the first length. In one embodiment, one or more of the first pins may have a different length than one or more of the second pins. In one embodiment, one or more of the first pins may have a different length than the remaining first pins. In one embodiment, one or more of the second pins may have a different length than the remaining second pins.

In one embodiment, the plate of the tissue anchor preferably has an array of second pin apertures that are offset from the first pins, whereby each second pin aperture has a diameter, and whereby each second pin aperture extends from the top surface to the bottom surface of the plate.

In one embodiment, the array of second pins extend through the second pin apertures. In one embodiment, each second pin has the elongated shaft having an upper end including a second barb facing away from the top surface of the plate and a lower end including a stop that is located below the bottom surface of the plate. In one embodiment, the elongated shafts of the second pins have outer diameters that are smaller than the diameters of the second pin apertures for allowing the elongated shafts of the second pins to slide within the second pin apertures. In one embodiment, the second barbs at the upper ends of the elongated shafts of the second pins and the stops at the lower ends of the elongated shafts of the second pins have outer diameters that are larger than the diameters of the second pin apertures.

In one embodiment, a tissue anchor may be coated with an antimicrobial agent, such as triclosan, for reducing and minimizing the risk of bacterial colonization, infection and complications. In one embodiment, any one of the components of a tissue anchor, such as a plate, one or more of the pins, and/or one or more of the barbs may be coated with an antimicrobial agent.

These and other preferred embodiments of the present invention will be described in more detail below.

BRIEF DESCRIPTION OF THE DRAWINGS

FIG. 1A-1 shows a magnified view of the tissue anchor shown in FIG. 1A.

FIG. 2A-1 shows a magnified view of the tissue anchor shown in FIG. 2A.

FIG. 2B shows the tissue anchor of FIG. 2A after being positioned between two tissue layers.

FIG. 2C shows the tissue anchor of FIG. 2B after a second tissue layer has been pressed toward a first tissue layer for advancing the bi-directional array of barbed pins into the tissue layers, in accordance with one embodiment of the present patent application.

FIG. 2C-1 shows a magnified view of one of the barbed pins and the locking element shown in FIGS. 2A and 2C.

DETAILED DESCRIPTION OF PREFERRED EMBODIMENTS

Figure 1A:
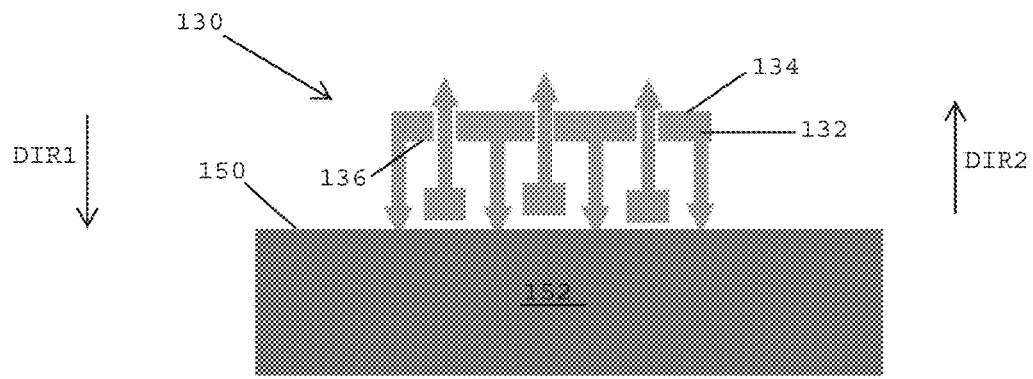
FIG. 1A shows a cross-sectional view of a tissue anchor having a bi-directional array of barbed pins for joining tissue layers, in accordance with one embodiment of the present patent application.
Figures 1, 1A:
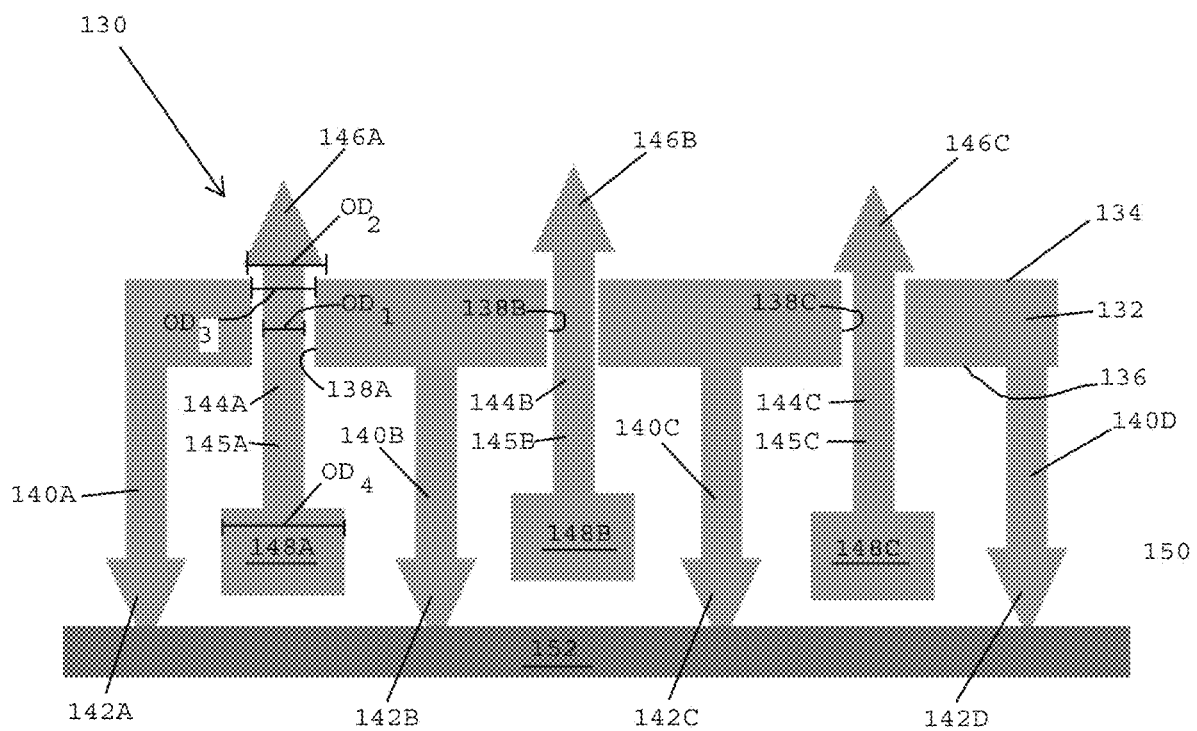

Referring to FIGS. 1A and 1A-1, in one embodiment, a tissue anchor 130 for joining tissue layers preferably includes a plate 132 having a top surface 134, a bottom surface 136 and a plurality of apertures 138A-138C that extend from the top surface 134 to the bottom surface 136. In one embodiment, the tissue anchor 130 desirably includes an array of elongated first pins 140A-40D having lower ends with tissue engaging barbs 142A-142D that face in a first direction DIR1, which is away from the bottom surface 136 of the plate 132. In one embodiment, the tissue anchor 130 desirably includes an array of elongated second pins 144A-144C having upper ends with respective tissue engaging barbs 146A-146C that face in an opposite, second direction DIR2, which is away from the top surface 134 of the plate 132. In one embodiment, each of the second pins 144A-144C has a lower end including a stop 148A-148C secured to the lower ends of the respective second pins. The stops 148A-148C are preferably blunt.

In one embodiment, each of the second pins 144A-144C is disposed within one of the spaced apertures 138A-138C of the plate 132. In one embodiment, the second pins 144A-144C have elongated shafts 145A-145C with cross-sectional diameters $OD_1$ that are smaller than the diameters $OD_2$ of the apertures 138A-138C. In one embodiment, the barbs 146A-146C at the upper ends of the elongated shafts 145A-145C have respective bases having outer diameters $OD_3$ that are larger than the diameters $OD_2$ of the plate apertures 138A-138C. In one embodiment, the stops 148A-148C at the lower ends of the elongated shafts 145A-145C have diameters $OD_4$ that are larger than the diameters $OD_2$ of the apertures 138A-138C formed in the plate 132. As a result, the elongated shafts 145A-145C of the second pins 144A-144C are free to slide and move within the apertures 138A-138C of the plate 132 in a direction that is perpendicular to the top and bottom surfaces 134, 136 of the plate 132. However, the larger sized diameters of the second barbs 146A-146C and the stops 148A-148C prevent the second pins 144A-144C from exiting or uncoupling from the apertures 138A-138B of the plate 132.

In one embodiment, the tissue anchor 130 is desirably utilized for joining tissue layers, such as two parallel tissue layers. In one embodiment, the tissue anchor 130 may be placed over a surface 150 of a first tissue layer 152. In one embodiment, during a deployment step of a surgical procedure, the first barbs 142A-142D of the first pins 140A-140D are desirably placed in contact with the top surface 150 of the first tissue layer 152.

In one embodiment, the spacing between each of the first pins 140A-140D is about 4-50 mm. In one embodiment, the spacing between each of the second pins 144A-144C is about 4-50 mm. In one embodiment, the spacing between the centers of each of the plate apertures 138A-138C desirably matches the spacing between the second pins 144A-144C.

In one embodiment, the tissue anchor 130 may be absorbable or non-absorbable. In one embodiment, one or more components of the tissue anchor 130 may be absorbable or non-absorbable.

Figure 1B:
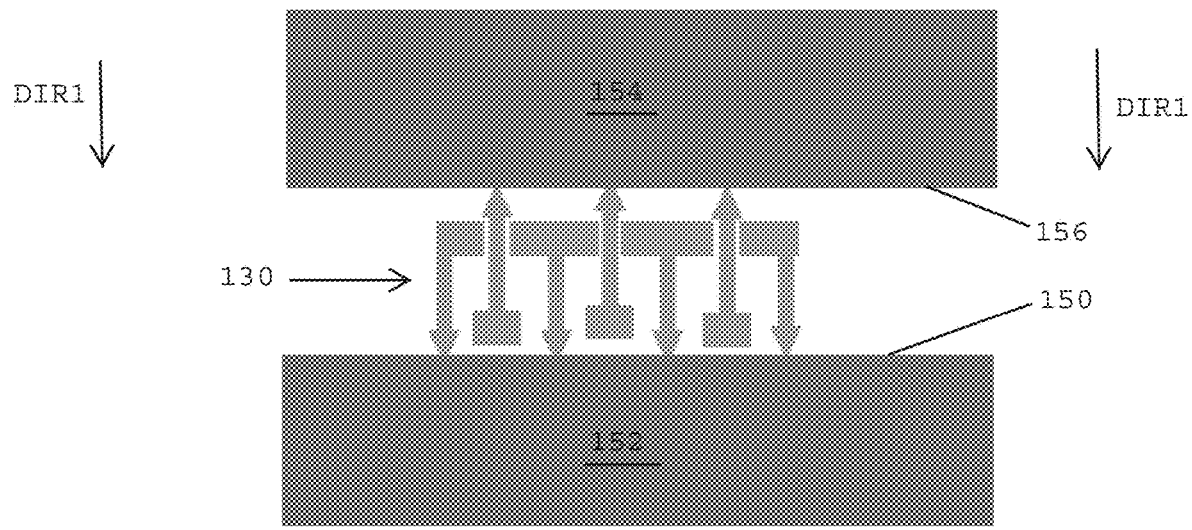
FIG. 1B shows the tissue anchor of FIG. 1A after being positioned between two tissue layers.

Referring to FIG. 1B, in one embodiment, after the tissue anchor 130 has been positioned on the top surface 150 of the first tissue layer 152, the tissue anchor 130 may be covered by a second tissue layer 154, whereby the second barbs 146A-146C of the second pins 144A-144C oppose and engage a bottom surface 156 of the second tissue layer 154.

In one embodiment, pressure is applied to the second tissue layer 154, preferably in the direction DIR1, to compress the second tissue layer onto the tissue anchor 130 and the first tissue layer 152.

Figure 1C:
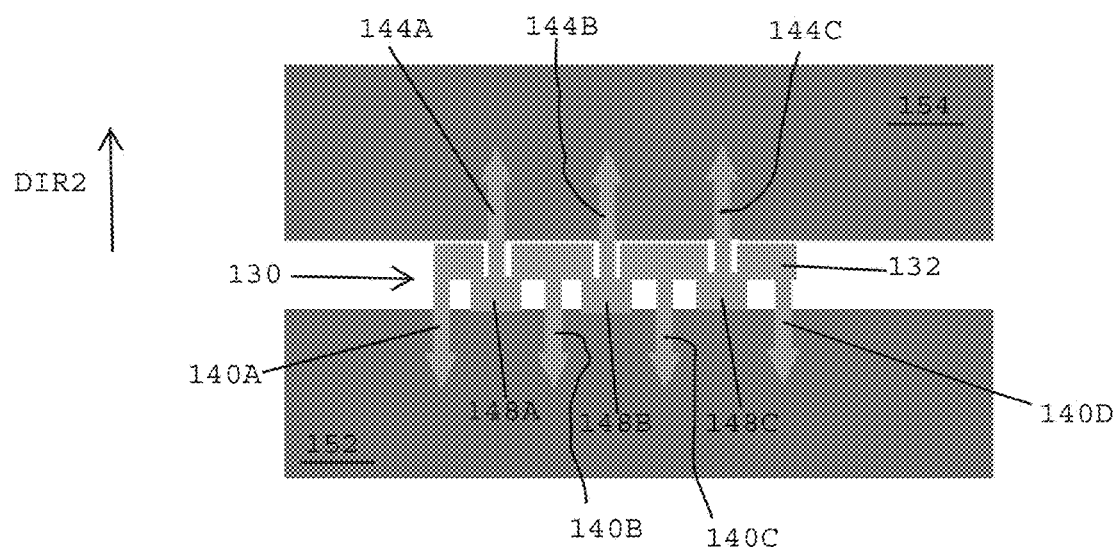
FIG. 1C shows the tissue anchor of FIG. 1B after a second tissue layer has been pressed toward a first tissue anchor for advancing the bi-directional array of barbed pins into the tissue layers, in accordance with one embodiment of the present patent application.

Referring to FIG. 1C, in one embodiment, as the second tissue layer 154 is pressed onto the first tissue layer 152, the first pins 14A-40D of the tissue anchor 130 desirably enter the first tissue layer 152 and the oppositely directed second pins 144A-144C of the tissue anchor 130 desirably enter the second tissue layer 154. As compression is applied to the second tissue layer 154, the second pins 144A-144C preferably slidably move through the apertures 138A-138C (FIG. 1A-1) of the plate 132 in the direction DIR2. The second pins 144A-144C continue to move in the direction DIR2 until the stops 144A-144C at the lower ends of the second pins 144A-144C abut against the bottom surface 136 of the plate 132 for halting further sliding movement of the second pins 144A-144C. The barbs on the respective first and second pins preferably bite into the first and second tissue layers 152, 154 for preventing the pins from retracting from the tissue.

In one embodiment, the tissue anchor 130 may be coated with an antimicrobial agent, such as triclosan, for reducing and minimizing the risk of bacterial colonization, infection, or complications. In one embodiment, any one of the components of a tissue anchor, such as the plate 132, one or more of the pins 142A-142D and 144A-144C, and/or one or more of the barbs 142A-142D and 146A-146C may be coated with an antimicrobial agent.

Figure 2A:
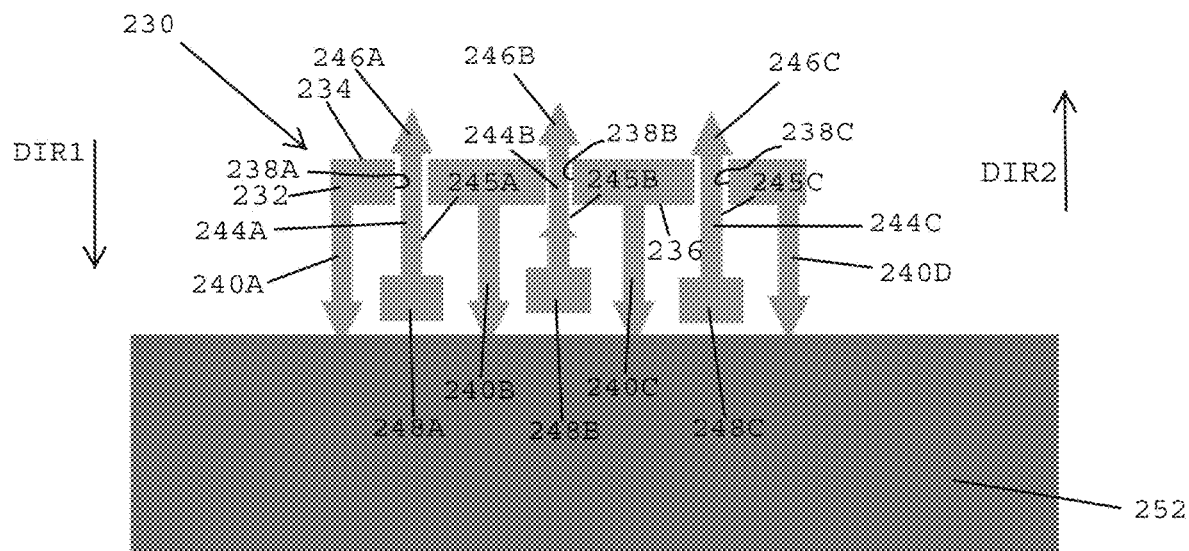
FIG. 2A shows a cross-sectional view of a tissue anchor having a bi-directional array of barbed pins for joining tissue layers with one of the barbed pins having a locking element, in accordance with one embodiment of the present patent application.
Figures 1, 2A:
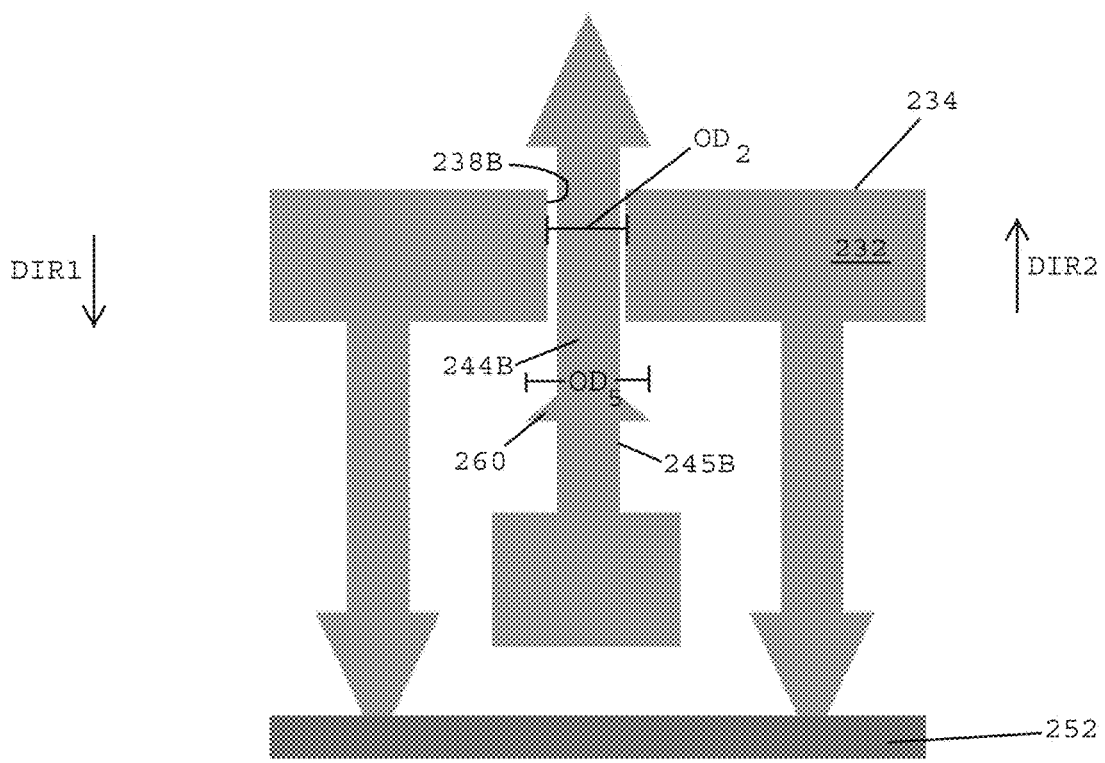

Referring to FIG. 2A, in one embodiment, a tissue anchor 230 for joining tissue layers preferably includes a plate 232 having a top surface 234, a bottom surface 236 and apertures 238A-238C extending from the top surface 234 to the bottom surface 236. The apertures 238A-238C are desirably spaced from one another over the area of the plate 232. In one embodiment, the tissue anchor 230 desirably includes an array of elongated first pins 240A-240D having lower ends with tissue engaging barbs 242A-242D, respectively, facing in a first direction DIR1.

The tissue anchor 230 desirably includes an array of elongated second pins 244A-244C having elongated shafts 245A-245C with upper ends having tissue engaging barbs 246A-246C that face in an opposite, second direction DIR2. The second pins 244A-244C preferably have stops 248A-248C at the lower ends of the elongated shafts 245A-245C. In one embodiment, the elongated shafts 245A-245C of the second pins 244A-244C have cross-sectional diameters that are smaller than the cross-sectional diameters of the openings 238A-238C formed in the plate 232. The barbs 246A-246C and the stops 248A-248C have respective outer diameters that are larger than the diameters of the apertures 238A-238C of the plate 132 so that the second pins 244A-244C are adapted to slide up and down in the apertures 238, while being limited by the size of the barbs 246A-246C and the stops 248A-248C from exiting the plate apertures 238A-238C.

Referring to FIGS. 2A and 2A-1, in one embodiment, one of the elongated second pins 244B preferably has a locking element 260 projecting outwardly from the elongated shaft 245B of the second pin 244B that locks the second pin in place and prevents the second pin from reversing direction. The locking element 260 preferably has an outer diameter $OD_5$ that is greater than the diameter $OD_2$ of the associated aperture 238B formed in the plate 232. The locking element 260 is preferably designed and configured so that the locking element 260 may pass through the aperture 238 as the elongated shaft 245B is moving in the direction designated DIR2, however, the locking element 260 prevents the elongated shaft 245B of the second pin 244B from moving in the opposite, second direction DIR1 once the locking element 260 has moved above the top surface 234 of the plate 232. The locking element 260 may be flexible and/or deformable for passing through the aperture 238B. The locking element 260 may produce an audible click or tactile feedback to medical personnel to provide an indication that the locking element 260 has move above the top surface 234 of the plate 232. In one embodiment, two or more of the second pins 244A-244C may have a locking element associated therewith.

Referring to FIG. 2B, in one embodiment, the tissue anchor 230 is desirably positioned between a first tissue layer 252 and an opposing second tissue layer 254. The first barbs 242A-242D of the first pins 240A-240D are desirably juxtaposed with a top surface 250 of the first tissue layer 252 and the second barbs 246A-246C of the second pins 244A-244C are preferably juxtaposed with the bottom surface 256 of the second tissue layer 254.

Referring to FIG. 2C, in one embodiment, in order to join the first and second tissue layers 252, 254, the second tissue layer 254 is compressed toward the first tissue layer 252 so that the elongated first pins 240A-240D enter the first tissue layer 252 and the elongated second pins 244A-244C enter the second tissue layer 254. As compression is applied to the tissue anchor 230, the second pins 244A-244C preferably slidably move in the direction DIR2 relative to the apertures 238A-238C formed in the plate 232.

Referring to FIGS. 2C and 2C-1, as the second pin 244B slides through aperture 238B of the plate 232 in the direction DIR2, the locking element 260 projecting outwardly from the elongated shaft 245B desirably moves above the top surface 234 of the plate 232 to lock the position of the elongated second pin 244B so that it may not reverse direction and move in the direction designated DIR1. In one embodiment, upward sliding movement of the second pins 244A-244C may be halted when the stops 248A-248C at the lower ends of the respective second pins 244A-244C abut against the bottom surface 236 of the plate 232. The locking element 260 preferably locks the tissue anchor 230 in the position shown in FIG. 2C and prevents the second pins 244A-244C from retracting relative to the plate 132. Although only one of the second pins 242B is shown as having the locking element 160, in other embodiments, two or more of the second pins 244A-244C (FIG. 2C) may have locking elements 160 projecting from elongated shafts thereof. In one embodiment, each of the second pins 244A-244C may have a locking element 260 for preventing reverse movement of the second pins 244A-244C after the locking elements 260 have slidably moved above the top surface 234 of the plate 232.

Figure 3:
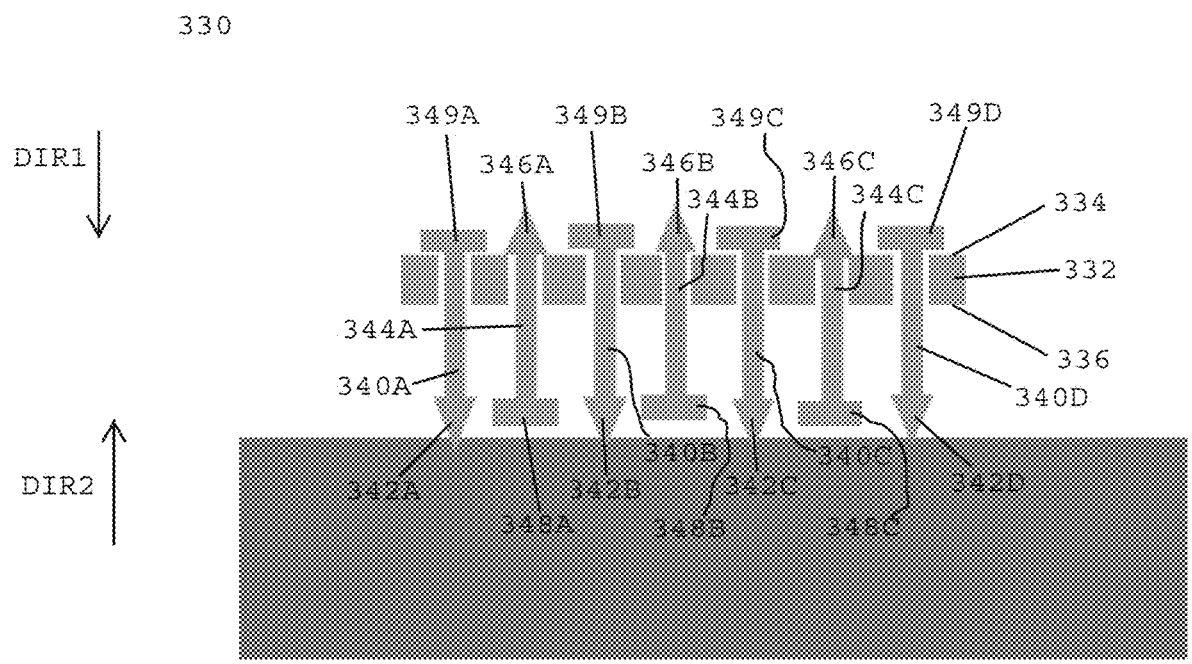
FIG. 3 shows a cross-sectional view of a tissue anchor having a bi-directional array of barbed pins for joining tissue layers, in accordance with one embodiment of the present patent application.

Referring to FIG. 3, in one embodiment, a tissue anchor 330 for joining tissue layers preferably includes a plate 332 having a top surface 334 and a bottom surface 336. In one embodiment, the plate 332 preferably includes an array of first pin apertures 338A-338D adapted to receive first pins 340A-340D and an array of second pin apertures 339A-339C adapted to receive second pins 344A-344C. The first and second pins are adapted to slidably move within the apertures. One or more of the pins may have a locking element as shown and described herein.

In one embodiment, the first pins 340A-340D preferably have lower ends with first barbs 342A-342D and upper ends with first stops 349A-349D. In one embodiment, the first pins 340A-340D are free to slide up and down within the first pin apertures 338A-338D formed in the plate 332. The sliding movement of the first pins is constrained by the first barbs 342A-342D and the first stops 349A-349D having larger diameters than the first pin apertures 238A-238D associated therewith.

In one embodiment, the tissue anchor 330 preferably includes second pins 344A-344C that are adapted to slide up and down within the second pin apertures 339A-339C of the plate 232. The second pins 344A-344C desirably have upper ends with barbs 346A-346C and lower ends with stops 348A-348C. The sliding movement of the second pins is constrained by the second barbs 346A-346C and the second stops 348A-348C having larger diameters than the second pin apertures 339A-339C associated therewith.

In one embodiment, the first stops 349A-349D on the first pins 340A-340D halt movement of the first pins in a direction DIR1 when the stops engage the top surface 334 of the plate 332. Similarly, the second stops 348A-348C on the second pins 344A-344C desirably halt movement of the pins in the direction DIR2 when the stops engage the bottom surface 336 of the plate 332.

Figure 4:
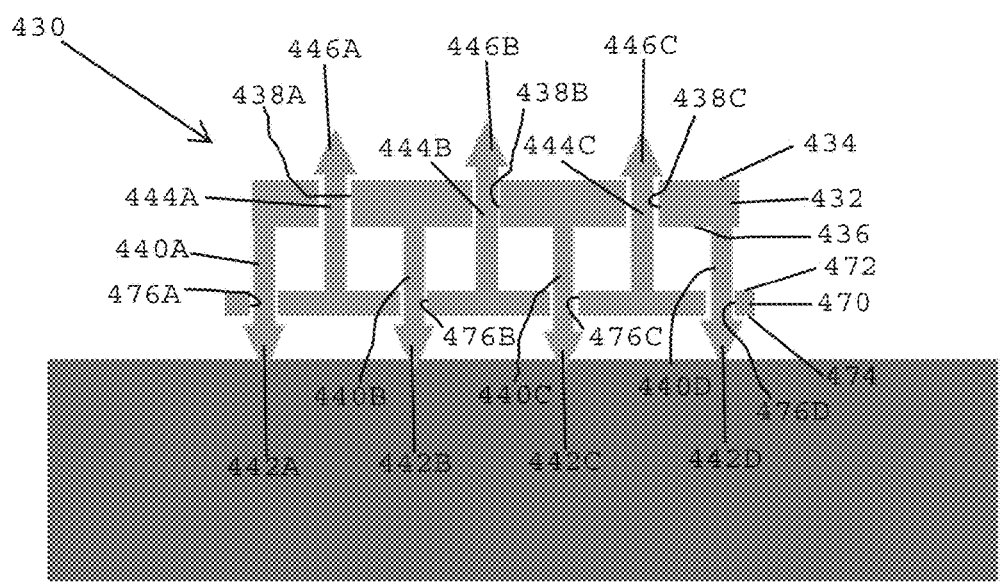
FIG. 4 shows a cross-sectional view of a tissue anchor having a bi-directional array of barbed pins for joining tissue layers, in accordance with one embodiment of the present patent application.

Referring to FIG. 4, in one embodiment, a tissue anchor 430 for joining two tissue layers desirably includes a first plate 432 having a top surface 434, a bottom surface 436, and apertures 438A-438C extending from the top surface 434 to the bottom surface 436 of the first plate 432. The tissue anchor 430 preferably includes an array of elongated first pins 440A-440D projecting downwardly from the bottom surface 436 of the first plate 432. In one embodiment, the first pins 440A-440D desirably include lower ends having tissue engaging barbs 442A-442D. In one embodiment, the upper ends of the elongated first pins 44A-440D are permanently affixed to the first plate 432.

In one embodiment, the tissue anchor 430 desirably includes a second plate 470 having a top surface 472 and a bottom surface 474 with spaced apertures 476A-476D extending from the top surface 472 to the bottom surface 474 of the second plate 470. The tissue anchor 430 desirably includes an array of elongated second pins 444A-444C having lower ends affixed to the second plate 470 and upper ends including tissue engaging barbs 446A-446C.

In one embodiment, the barbs 442A-442D on the first pins 440A-440D have a larger outer diameter than the spaced apertures 476A-476D formed in the second plate 470 so that the first plate 432 may not be separated from being coupled with the second plate 470. Similarly, in one embodiment, the barbs 446A-446C on the second pins 444A-444C have larger outer diameters than the spaced apertures 438A-438C provided in the first plate 432 so that the first plate 432 may not be uncoupled from its connection with the second plate 430. The tissue anchor 430 may be positioned between adjacent tissue layers for joining the tissue layers together.

Figure 5A:
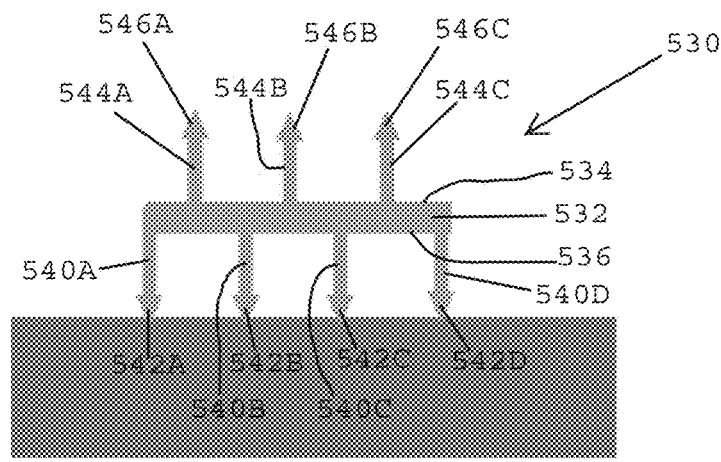
FIG. 5A shows a cross-sectional view of a tissue anchor having a bi-directional array of barbed pins for joining tissue layers, in accordance with one embodiment of the present patent application.

Referring to FIG. 5A, in one embodiment, a tissue anchor 530 for joining tissue layers, such as two parallel tissue layers, preferably includes a plate 532 having a top surface 534 and a bottom surface 536 facing away from the top surface 534. In one embodiment, the top and bottom surfaces 534, 536 are flat. In one embodiment, the top and bottom surfaces 534, 536 are parallel to one another.

In one embodiment, the tissue anchor 530 preferably includes an array of elongated first pins 540A-540D having upper ends affixed to the bottom surface 536 of the plate 532 and lower ends having tissue engaging barbs 542A-542D.

In one embodiment, the tissue anchor 530 desirably includes an array of elongated second pins 544A-544C having lower ends secured to the top surface 534 of the plate 532 and upper ends including tissue engaging barbs 546A-546C. In one embodiment, the location of the first pins 540A-540D is offset from the location of the second pins 544A-544C (i.e., the first pins are not in axial alignment with the second pins). Although the tissue anchor 530 shown in FIG. 5A has four first pins 54A-540D and three second pins 544A-544C, other embodiments may have more or fewer less first and second pins and still fall within the scope of the claimed invention.

Figure 5B:
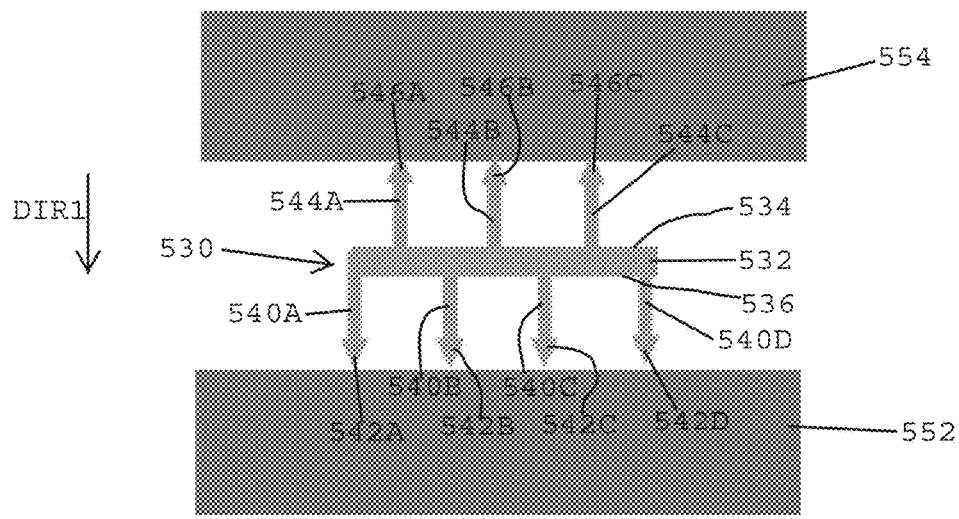
FIG. 5B shows the tissue anchor of FIG. 5A after being positioned between two tissue layers.

Referring to FIG. 5B, in one embodiment, the tissue anchor 530 may be juxtaposed between a first tissue layer 552 and a second tissue layer 554. In one embodiment, the tissue anchor 530 may be positioned atop of the first tissue layer 552 so that the first barbs 542A-542D of the respective first pins 540A-540D abut against the first tissue layer 552, and the second barbs 546A-546C of the respective second pins 544A-544C abut against the second tissue layer 554. In one embodiment, a plurality of tissue anchors 530 may be positioned between the first and second tissue layers 552, 554 for joining the tissue layers together.

Figure 5C:
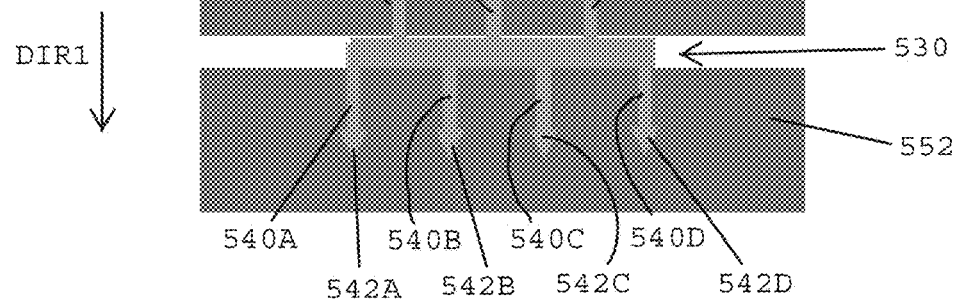
FIG. 5C shows the tissue anchor of FIG. 5B after a second tissue layer has been pressed toward a first tissue layer for advancing the bi-directional array of barbed pins into the tissue layers, in accordance with one embodiment of the present patent application.

Referring to FIGS. 5B and 5C, in one embodiment, the second tissue layer 554 is pressed toward the first tissue layer 552 in the direction DIR1 so that the first barbs 542A-542D of the first pins 540A-540D enter the first tissue layer and the second barbs 546A-546C of the second pins 544A-544C enter the second tissue layer 554.

Referring to FIG. 5C, the first and second tissue layers 552, 554 are held together by the tissue anchor 530. The barbs on the respective first and second pins prevent the pins from retracting from the tissue.

Figure 6A:
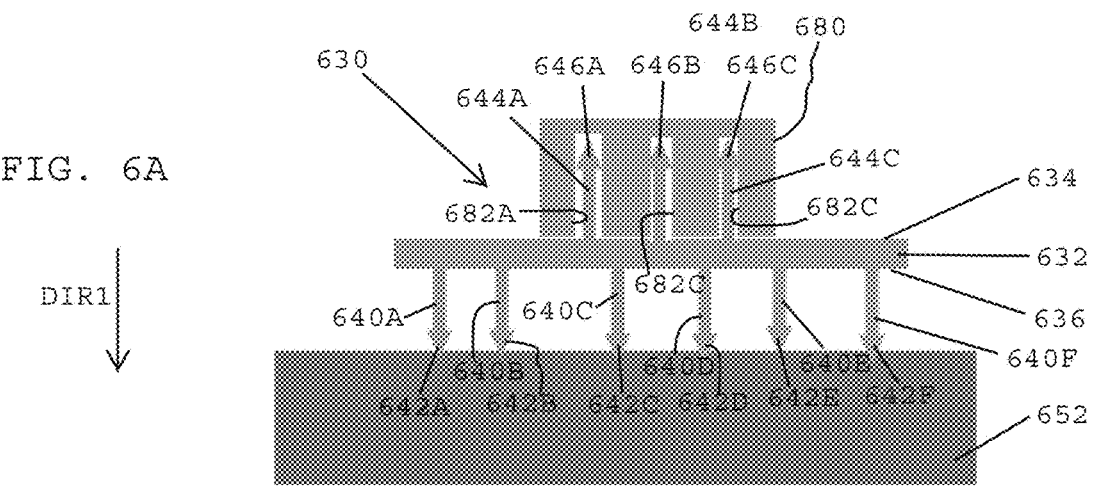
FIG. 6A shows a cross-sectional view of a tissue anchor having a bi-directional array of barbed pins for joining tissue layers and a safety cap covering the barbed pins projecting from a top surface of a plate, in accordance with one embodiment of the present patent application.

Referring to FIG. 6A, in one embodiment, a tissue anchor 630 preferably includes a plate 632 having a top surface 634 and a bottom surface 636 that faces away from the top surface 634. In one embodiment, the tissue anchor 630 includes first pins 640A-640F that project away from the bottom surface 636 of the plate 632. The first pins 640A-640F desirably have lower ends with barbs 642A-642F.

In one embodiment, the tissue anchor 630 preferably includes an array of elongated second pins 644A-644C having upper ends with respective second barbs 646A-646C. In one embodiment, the array of elongated first pins 640A-640F are preferably offset from the array of elongated second pins 644A-644C so that the first and second pins are not in alignment with one another.

In one embodiment, the tissue anchor 630 preferably includes a safety cap 680 having apertures 682A-682C that are open at the bottom of the safety cap 680 and that are adapted to cover the elongated second pins 644A-644C prior to deployment between tissue layers.

Figure 6B:
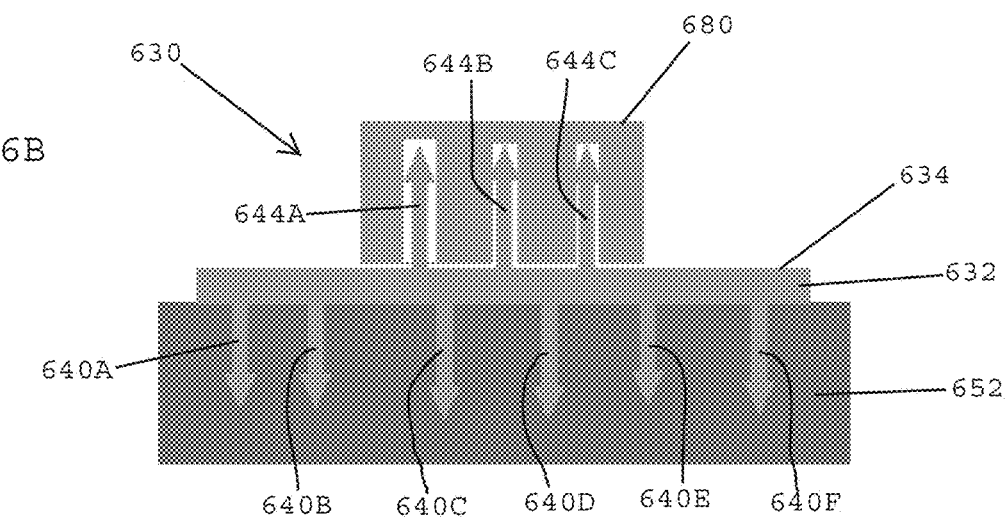
FIG. 6B shows the tissue anchor of FIG. 6A after the barbed pins projecting from the bottom surface of the plate have been advance into a first tissue layer.

Referring to FIGS. 6A and 6B, in one embodiment, the safety cap 680 initially covers the second elongated pins 644A-644C projecting upwardly from the top surface 634 of the plate 632. The tissue anchor 630 is preferably positioned atop a first tissue layer 652 with the first barbs 642A-642F engaging the first tissue layer 652. The safety cap 680 may be utilized to apply pressure to the tissue anchor 630 (in the direction DIR1) to drive the array of first elongated pins 640A-640F into the first tissue layer 652.

Figure 6C:
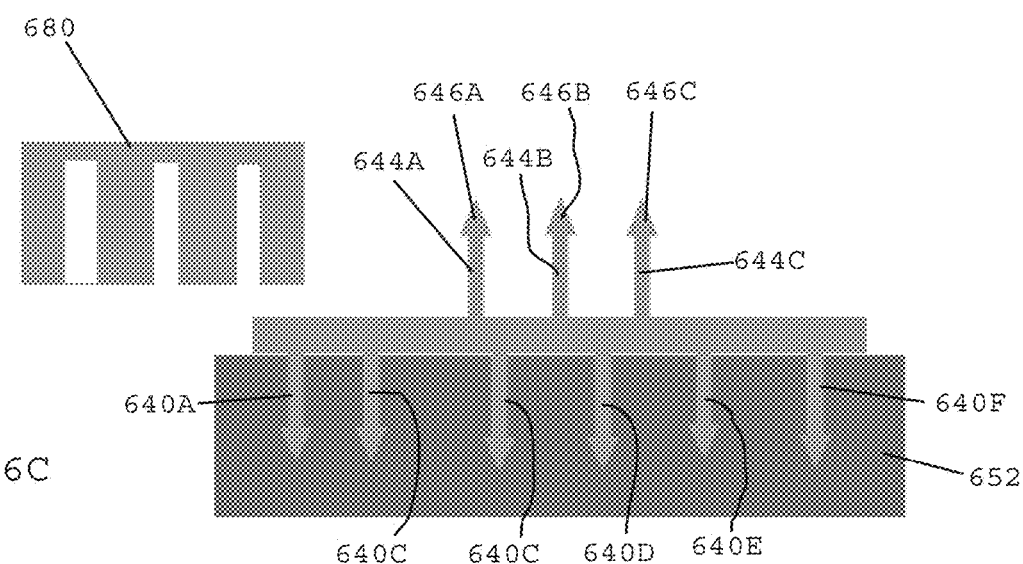
FIG. 6C shows the tissue anchor of FIG. 6B after the safety cap has been removed to expose the barbed pins projecting from the top surface of the plate, in accordance with one embodiment of the present patent application.

Referring to FIG. 6C, once the first elongated pins 640A-640F of the tissue anchor 630 have been driven into the first tissue layer 652, the safety cap 680 may be removed to expose the second elongated pins 644A-644C including the second tissue engaging barbs 646A-646C.

Figure 6D:
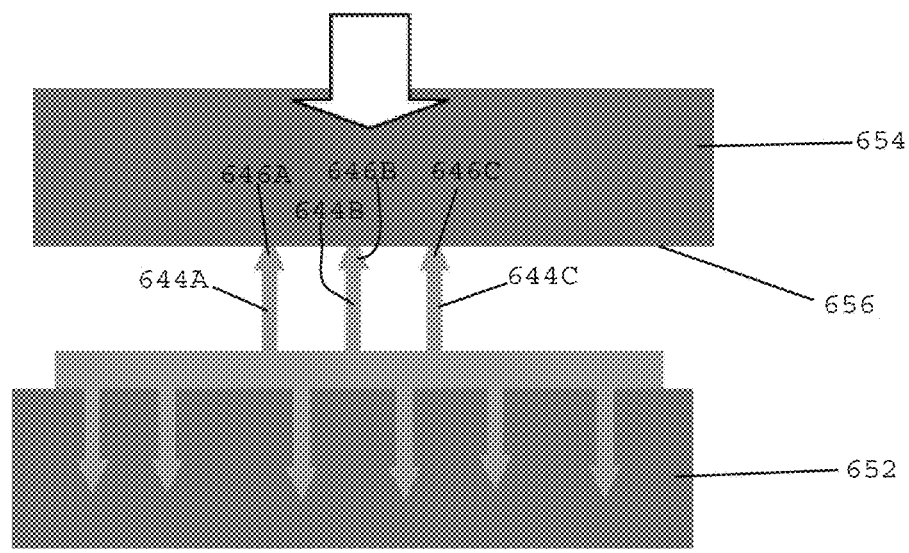
FIG. 6D shows the tissue anchor of FIG. 6C after a second tissue layer has been positioned atop the barbed pins projecting from the top surface of the plate.

Referring to FIG. 6D, in one embodiment, a second tissue layer 654 may be juxtaposed over the tissue anchor 630 and the first tissue layer 652 with the second barbs 646A-646C of the second pins 644A-644C facing toward the bottom surface 656 of the second tissue layer 654.

Figure 6E:
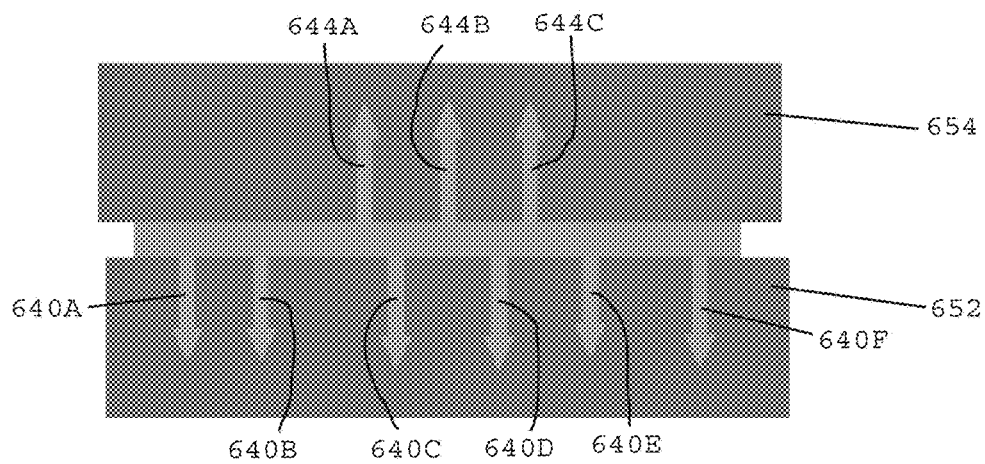
FIG. 6E shows the tissue anchor of FIG. 6D after the second tissue layer has been pressed toward the a first tissue layer for advancing the bi-directional array of barbed pins into the tissue layers, in accordance with one embodiment of the present patent application.

Referring to FIGS. 6D and 6E, in one embodiment, pressure may be applied to the second tissue layer 654 for driving the second pins 644A-644C into the second tissue layer. The first and second barbs on the respective first and second pins 640A-640F, 644A-644C preferably join the first and second tissue layers 652, 654 together and prevent the pins from retracting from the tissue layers.

Figure 7A:
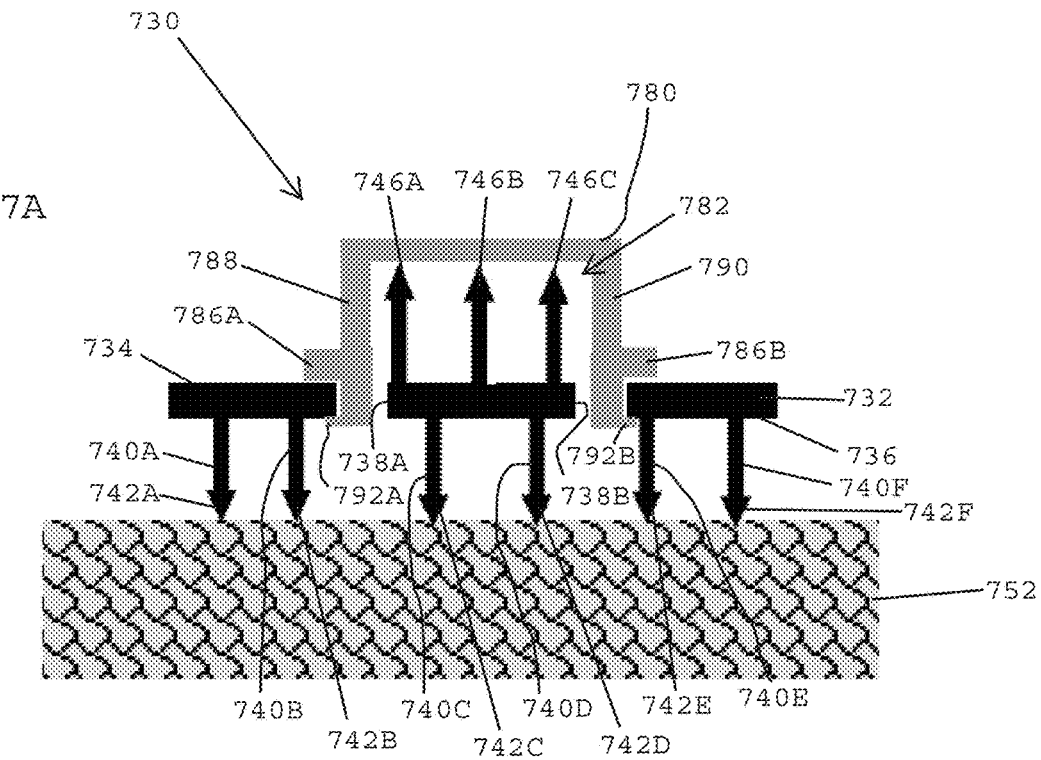
FIG. 7A shows a cross-sectional view of a tissue anchor having a bi-directional array of barbed pins for joining tissue layers and a safety cap covering the barbed pins projecting from a top surface of a plate, in accordance with one embodiment of the present patent application.

Referring to FIG. 7A, in one embodiment, a tissue anchor 730 for joining tissue layers preferably includes a plate 732 having a top surface 734, a bottom surface 736 and first and second spaced apertures 738A, 738B extending from the top surface to the bottom surface of the plate 732. In one embodiment, the tissue anchor 730 desirably includes an array of first pins 740A-740F projecting from the bottom surface 736 of the plate 732. Each of the first pins 740A-740F preferably has a tissue engaging barb 742A-742F associated therewith. In one embodiment, the tissue anchor 730 desirably includes an array of elongated second pins 744A-744C projecting upwardly from the top surface 734 of the plate 732. Each of the second pins 744A-744C preferably has a tissue engaging barb 746A-746C associated therewith. In one embodiment, the tissue anchor 730 desirably includes a safety cap 780 having a central opening 782 adapted to cover the upper ends of the second pins 744A-744C prior to deployment of the tissue anchor 730. In one embodiment, the safety cap 780 includes a first attachment flange 786A provided at a lower end of a first side wall 788 of the safety cap and a second attachment flange 786B provided at a lower end of a second side wall 790 of the safety cap 780. In one embodiment, the first and second attachment flanges 786A, 786B preferably engage with the respective aperture 738A, 738B of the plate 732 for releasably securing the safety cap 780 in place over the top surface 734 of the plate 732. The lower ends of the two side walls 788, 790 may be pressed inwardly from one another for removing the safety cap 780 from a releasably attachment with the plate 732.

Figure 7B:
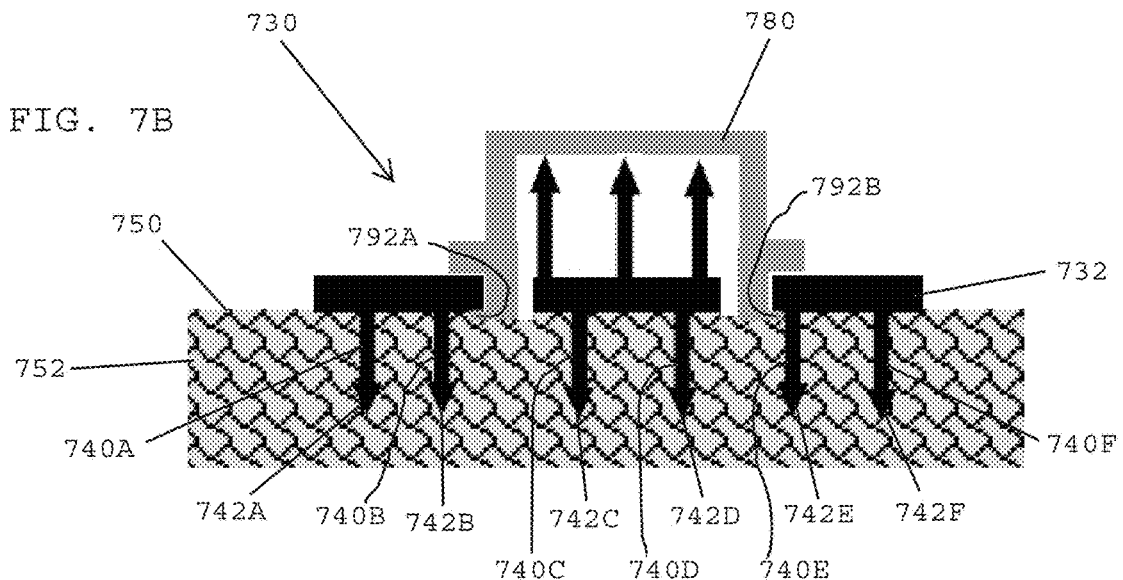
FIG. 7B shows the tissue anchor of FIG. 7A after the barbed pins projecting from the bottom surface of the plate have been advance into a first tissue layer.

Referring to FIGS. 7A and 7B, in one embodiment, the tissue anchor 730 is preferably positioned over a top surface 750 of a first tissue layer 752. The first barbs 742A-742F are preferably positioned in contact with the top surface 750 of the first tissue layer 752. Pressure may be applied to the safety cap 780 and/or the plate 732 for driving the first pins 740A-740F into the first tissue layer 752.

Figure 7C:
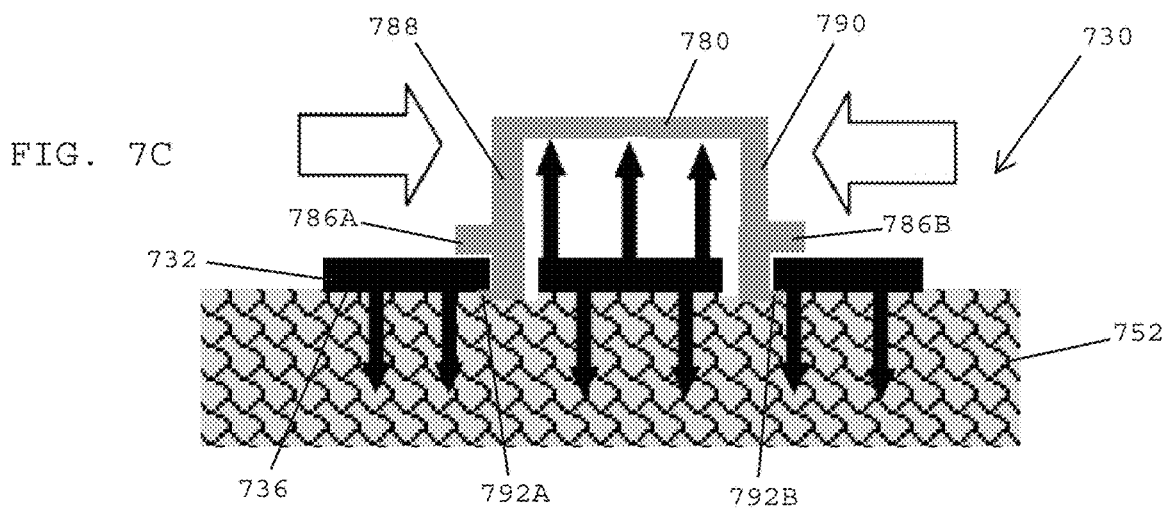
FIG. 7C shows the tissue anchor of FIG. 7B as the side walls of the safety cap are being pressed inwardly for removing the safety cap to expose the barbed pins projecting from the top surface of the plate, in accordance with one embodiment of the present patent application.
Figure 7D:
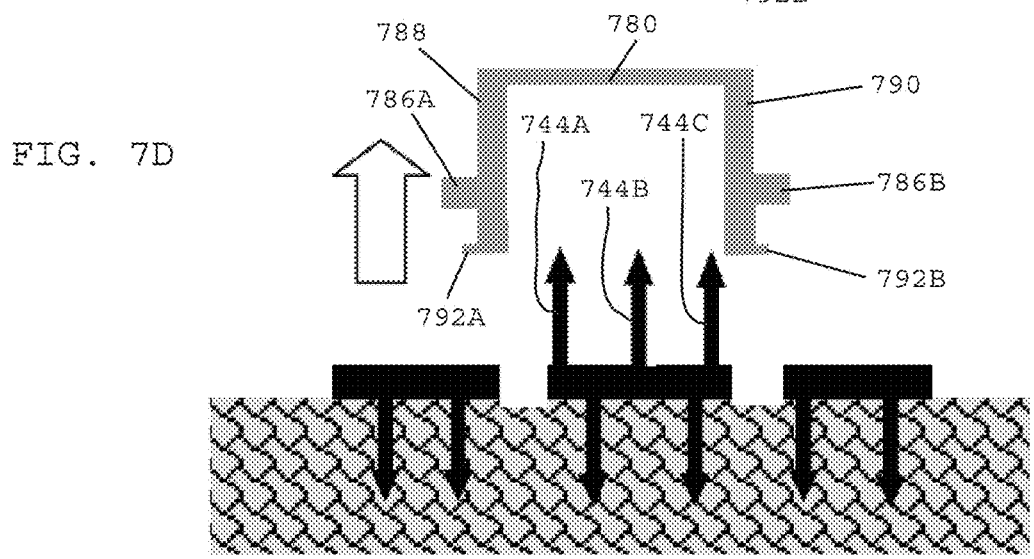
FIG. 7D shows the tissue anchor of FIG. 7C after the safety cap has been removed for exposing the barbed pins projecting from the top surface of the plate, in accordance with one embodiment of the present patent application.

Referring to FIGS. 7C and 7D, in one embodiment, after the tissue anchor 730 has been driven into the first tissue layer 752, the safety cap 780 may be removed by pressing the attachment flanges 786A, 786B inwardly toward one another for compressing the lower ends of the respective sidewall 788, 790 toward one another. As the attachment flanges 786A, 786B are pressed inwardly toward one another, lower ledges 792A, 792B of the attachment flanges are freed from their engagement with the bottom surface 736 of the plate 732 so that the safety cap 780 may be lifted up and away from the plate 732 (FIG. 6D) to expose the second pins 744A-744C.

Figure 7E:
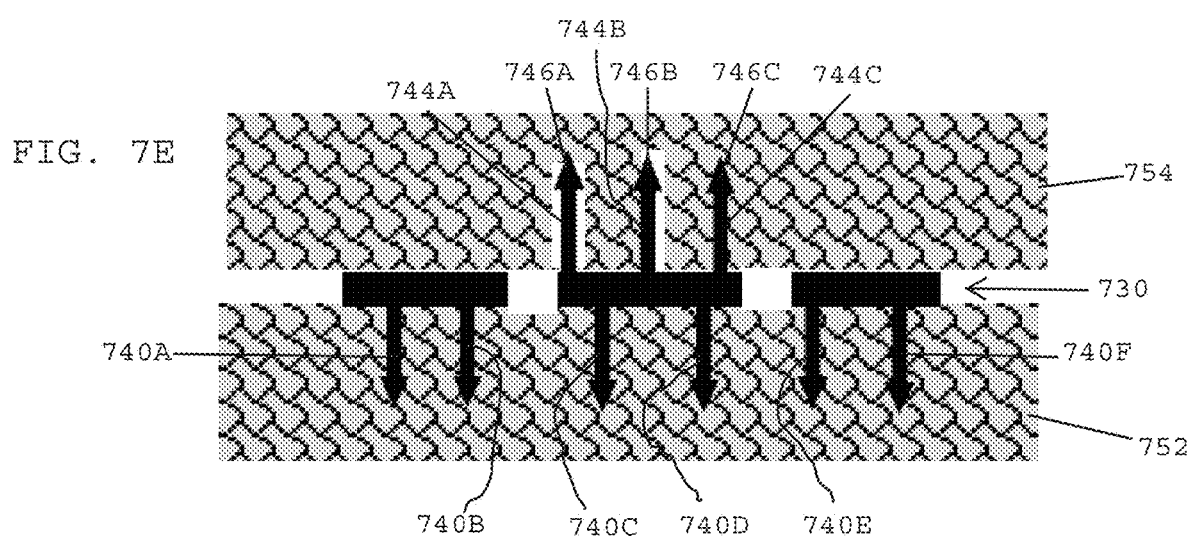
FIG. 7E shows the tissue anchor of FIG. 7D after the second tissue layer has been pressed toward the a first tissue layer for advancing the bi-directional array of barbed pins into the tissue layers, in accordance with one embodiment of the present patent application.

Referring to FIGS. 7D and 7E, in one embodiment, after the safely cap 780 has been removed, the second barbs 746A-746C at the upper ends of the second pins 744A-744C are exposed for being driven into a second tissue layer 754, which is preferably pressed onto the top of the tissue anchor 730. Referring to FIG. 7E, in one embodiment, the first pins 74A-740F are preferably advanced into the first tissue layer 752 and the second pins 744A-744C are preferably advanced into the second tissue layer 754 for joining the two tissue layers together.

Figure 8:
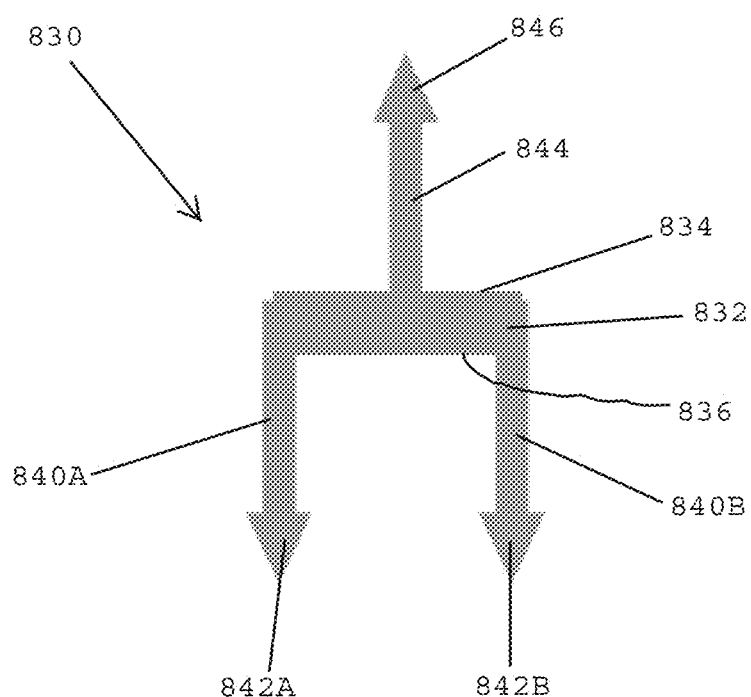
FIG. 8 shows a tissue anchor having a bi-directional array of barbed pins for joining tissue layers, in accordance with one embodiment of the present patent application.

Referring to FIG. 8, in one embodiment, a tissue anchor 830 desirably includes a plate 832 having a top surface 834 and a bottom surface 836 facing away from the top surface. In one embodiment, the tissue anchor 830 desirably includes first pins 840A, 840B that project downwardly from the bottom surface 836 of the plate 832. The lower ends of the first pins 840A, 840B desirably include tissue engaging barbs 842A, 842B for piercing tissue and holding the first pins within the tissue. In one embodiment, the tissue anchor 830 desirably includes an elongated second pin 844 projecting upwardly from the top surface 834 of the plate 832. An upper end of the elongated second pin 844 preferably includes a tissue engaging barb 846 for biting into tissue. The tissue anchor 830 shown in FIG. 8 may be deployed as shown and described herein in other embodiments. In one embodiment, the first pins 840A, 840B projecting from the bottom surface 836 of the plate 832 are preferably offset from the second pin 844 projecting from the top surface 834 of the plate 832.

Figure 9:
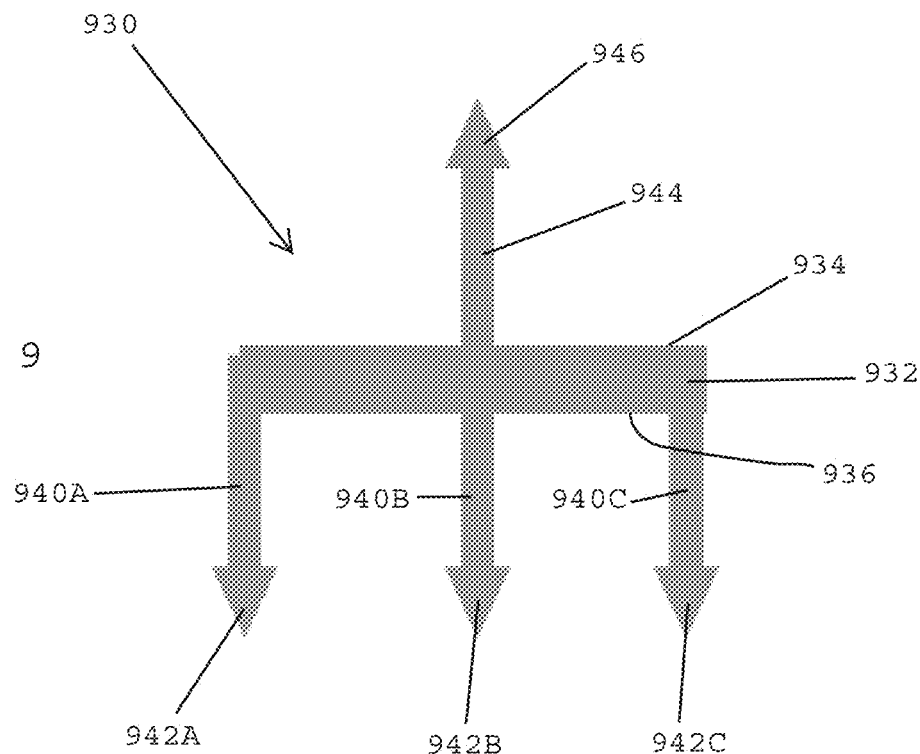
FIG. 9 shows a tissue anchor having a bi-directional array of barbed pins for joining tissue layers, in accordance with one embodiment of the present patent application.

Referring to FIG. 9, in one embodiment, a tissue anchor 930 preferably includes a plate 932 having a top surface 934 and bottom surface 936 that faces away from the top surface. In one embodiment, the tissue anchor 930 includes an array of first pins 94A-940C that project away from the bottom surface 936 of the plate 932. Each of the first pins 940A-940C preferably includes a tissue engaging barb 942A-942C provided at a lower end thereof. In one embodiment, the tissue anchor 930 desirably includes an elongated second pin 944 projecting upwardly from the top surface 934 of the plate 932. The second pin 944 has an upper end including a tissue engaging barb 946. In one embodiment, the second pin 944 is offset from two of the first pins 940A, 940C, but is in substantial alignment with a central one of first pins 940B. The tissue anchor 930 shown in FIG. 9 may be deployed as described herein for other embodiments.

Figure 10:
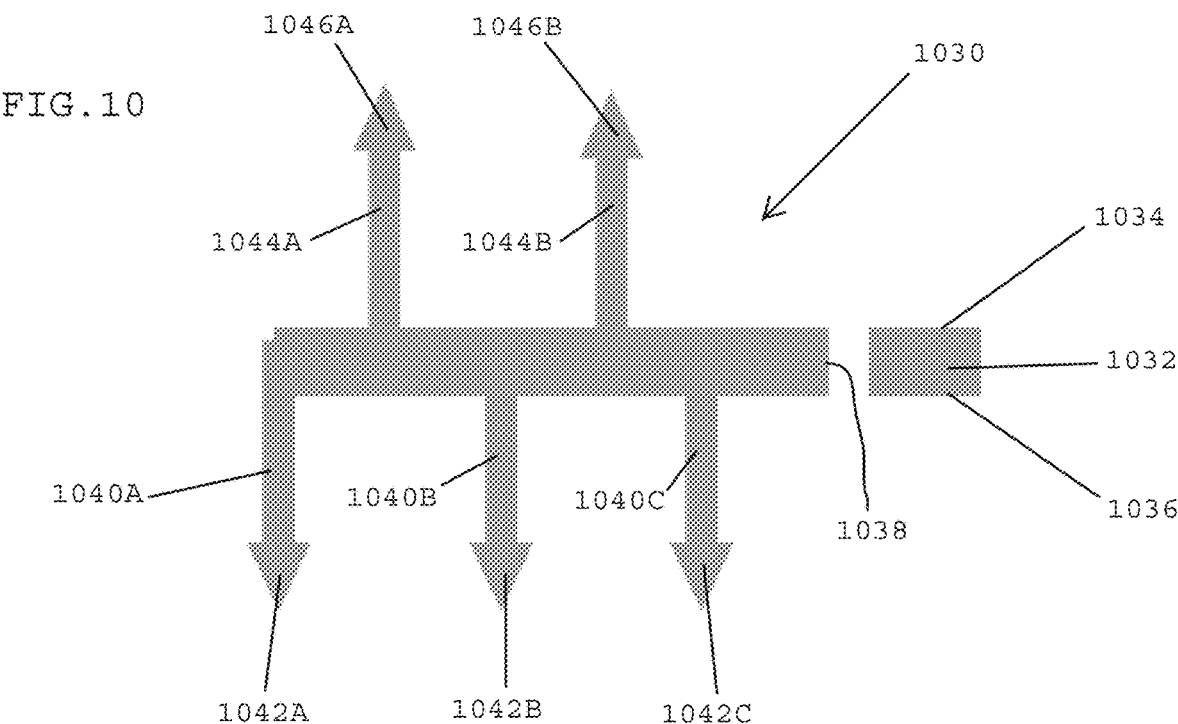
FIG. 10 shows a tissue anchor having a bi-directional array of barbed pins for joining tissue layers, in accordance with one embodiment of the present patent application.

Referring to FIG. 10, in one embodiment, a tissue anchor 1030 desirably includes a plate 1032 having a top surface 1034 and a bottom surface 1036. In one embodiment, the plate 1032 may include an aperture 1038 that extends from the top surface 1034 to the bottom surface 1036 thereof. In one embodiment, the tissue anchor 1030 desirably includes an array of first pins 1040A-1040C that extend downwardly from the bottom surface 1036 of the plate 1032. In one embodiment, lower ends of each of the first pins 104A-1040C has a respective barb 1042A-102C attached thereto for engaging tissue.

In one embodiment, the tissue anchor 1030 desirably includes an array of second pins 1044A-1044B that project upwardly from the top surface 1034 of the plate 1032. Each of the respective second pins 1044A-1044B has a tissue engaging barb 1046A-1046B secured thereto. In one embodiment, the aperture 1038 may be utilized for temporarily securing a safety cap over the top surface 1034 of the plate as shown and described above in FIGS. 7A-7E. In one embodiment, the array of first pins 1040A-1040C are offset from the array of second pins 1044A-1044B so that the first and second pins are not in axial alignment with one another.

Figure 11:
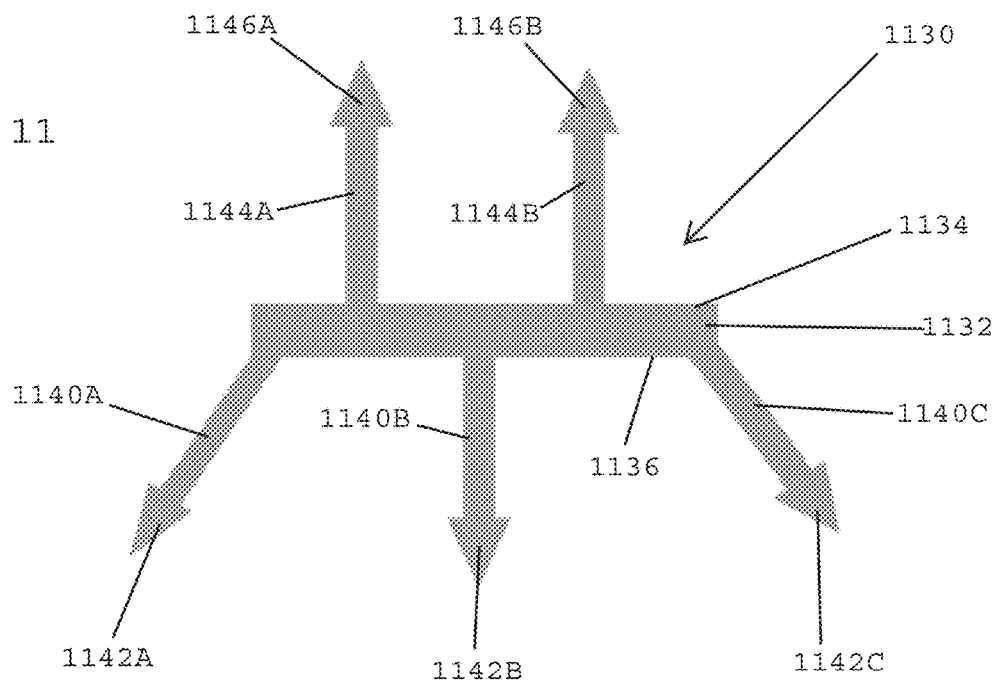
FIG. 11 shows a tissue anchor having a bi-directional array of barbed pins for joining tissue layers, in accordance with one embodiment of the present patent application.

Referring to FIG. 11, in one embodiment, a tissue anchor 1130 preferably includes a flat plate 1132 having a flat top surface 1134 and a flat bottom surface 1136. In one embodiment, the tissue anchor 1130 desirably includes an array of first pins 1140A-1140C that project from the bottom surface 1136 of the plate 1132. Each of the array of first pins 1140A-1140C preferably has a lower end including a tissue engaging barb 1142A-1142C. In one embodiment, the middle one of the elongated first pins 1140B is perpendicular to the flat bottom surface 1136 of the plate 1132, however, the outer first pins 1140A and 1140C preferably extend away from the bottom surface 1136 of the plate 1132 along axes that are not perpendicular with the flat bottom surface 1136 of the plate 1132.

In one embodiment, the tissue anchor 1130 desirably includes array of second pins 1140A-1140B that project upwardly from the top surface 1134 of the plate 1132. The second pins 1144A, 1144B desirably have upper ends including tissue engaging barbs 1146A, 1146B for engaging a tissue layer.

Figure 12:
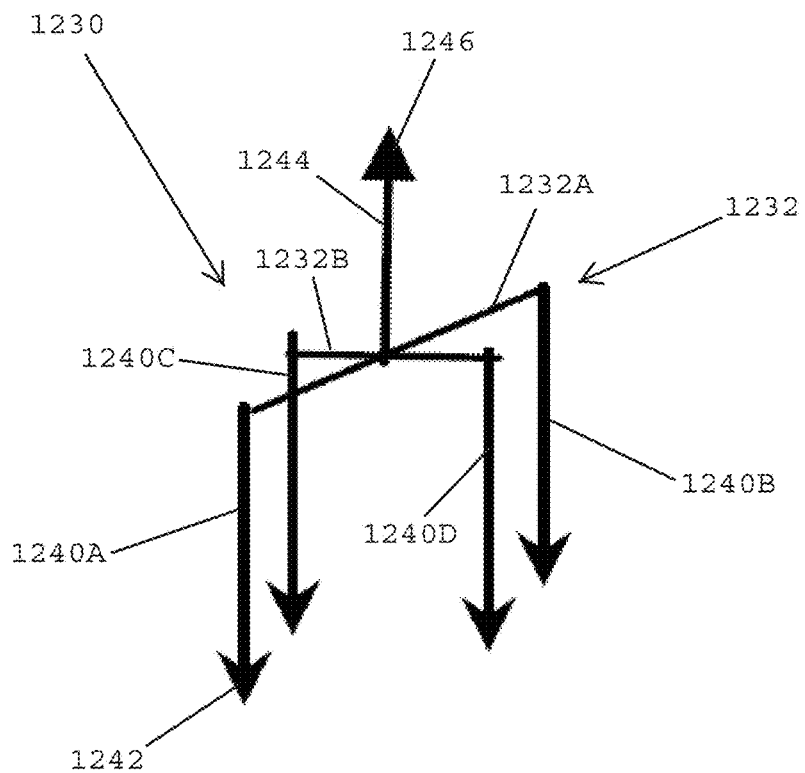
FIG. 12 shows a tissue anchor having a bi-directional array of barbed pins for joining tissue layers, in accordance with one embodiment of the present patent application.

Referring to FIG. 12, in one embodiment, a tissue anchor 1230 for joining tissue layers preferably has a cruciform shaped base 1232 including a first horizontally extending member 1232A and a second horizontally extending member 1232B that crosses the first horizontally extending member 1232A. In one embodiment, the tissue anchor 1230 includes a pair of pins 1240A, 1240B that extend downwardly from the first horizontally extending member 1232A, and second pair of pins 1240C and 1240D that extend downwardly from the second horizontally extending member 1232B. Each of the pins 1240A-1240D desirably has a tissue engaging barb provided at a lower end thereof. In one embodiment, the tissue anchor 1230 preferably includes a second pin 1244 that projects upwardly from a location where the first and second horizontally extending members 1232A, 1232B intersect one another. The second pin 1244 preferably has a tissue engaging barb 1246 attached to an upper end thereof.

Figure 13:
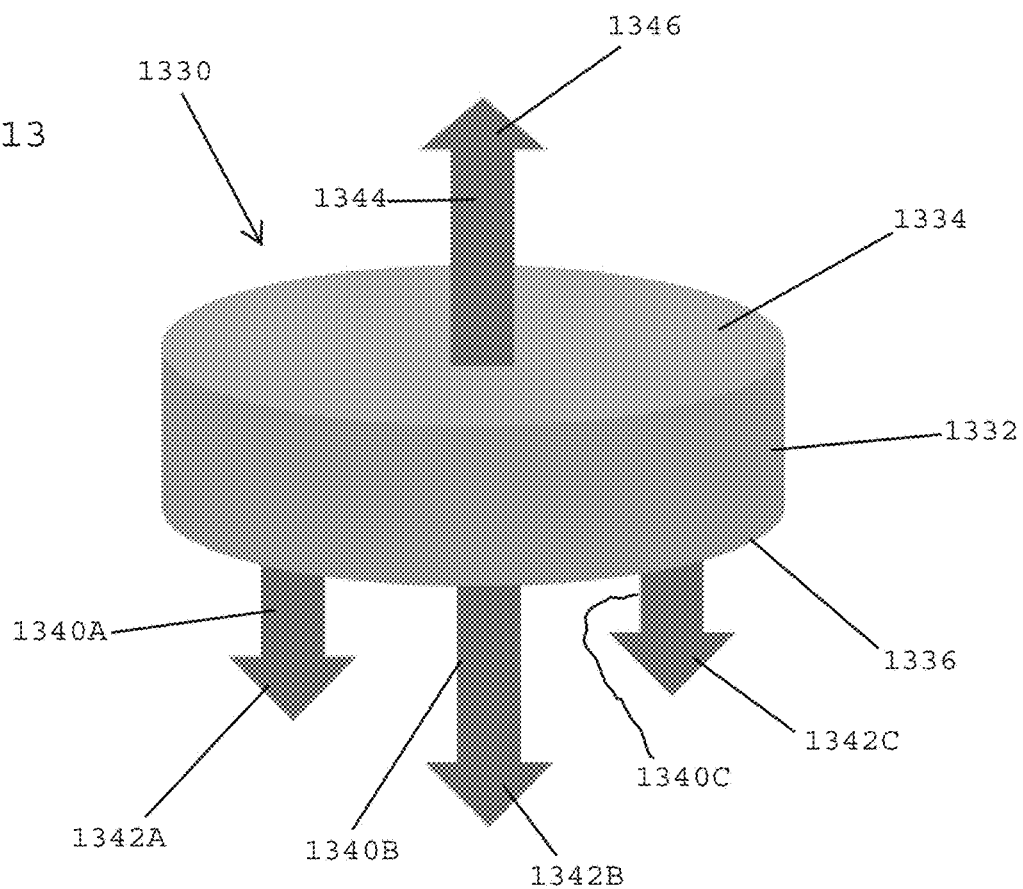
FIG. 13 shows a tissue anchor having a bi-directional array of barbed pins for joining tissue layers, in accordance with one embodiment of the present patent application.

Referring to FIG. 13, in one embodiment, a tissue anchor 1330 preferably includes a plate 1332 having a top surface 1334 and a bottom surface 1336. In one embodiment, the tissue anchor 1330 desirably includes an array of first pins 134A-1340C that project from the bottom surface 1336 of the plate 1332. Each of the array of the first pins 1340A-1340C has a tissue engaging barb 1342A-1342C attached thereto at a lower end thereof. In one embodiment, the tissue anchor 1330 desirably includes an elongated second pin 1344 that projects away from the top surface 1334 of the plate 1332. The elongated second pin 1344 has an upper end including a tissue engaging barb 1346 attached thereto. The tissue anchor 1330 may be deployed first and second tissue layers for joining the tissue layers together. In one embodiment, a plurality of the tissue anchors 1330 are deployed onto a top surface of a first tissue layer and a second tissue layer is pressed onto the prepositioned tissue anchors for joining the first and second tissue layers together.

The tissue anchors disclosed herein include a plate having one or more elongated first pins projecting from the bottom of the plate and one or more second pins projecting from the top side of the plate. When viewed from above, the plates of the tissue anchors may have different shapes and/or configurations.

Figure 14:
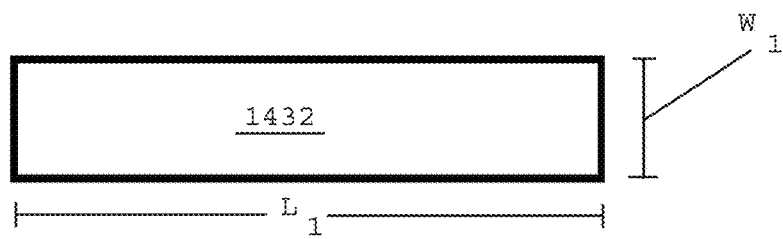
FIG. 14 shows a top plan view of a plate for a tissue anchor for joining tissue layers, in accordance with one embodiment of the present patent application.

Referring to FIG. 14, in one embodiment, a plate 1432 for a tissue anchor may have a rectangular shape having a length $L_1$ of about 1-10 cm and a width $W_1$ of about 0.3-2.0 cm.

Figure 15:
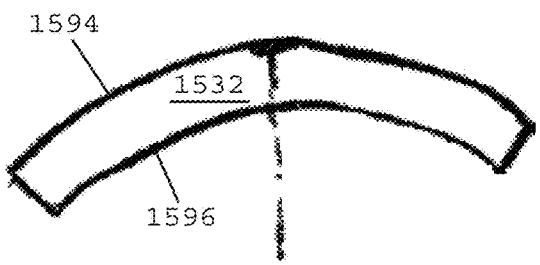
FIG. 15 shows a top plan view of a plate for a tissue anchor for joining tissue layers, in accordance with one embodiment of the present patent application.

Referring to FIG. 15, in one embodiment, a plate 1532 for a tissue anchor may have a curved shape including a convexly curved outer edge 1594 and a concave curved inner edge 1596. In one embodiment, the convexly curved outer edge 1594 may be defined as an arc of a circle having a radius $R_1$ of about 3-10 cm.

Figure 16:
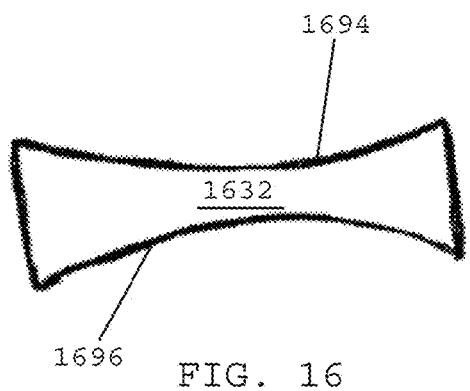
FIG. 16 shows a top plan view of a plate for a tissue anchor for joining tissue layers, in accordance with one embodiment of the present patent application.

Referring to FIG. 16, in one embodiment, a plate 1632 for a tissue anchor may have a first concave edge 1694 and a second concave edge 1696 that faces away from the first concave edge 1694.

Figure 17:
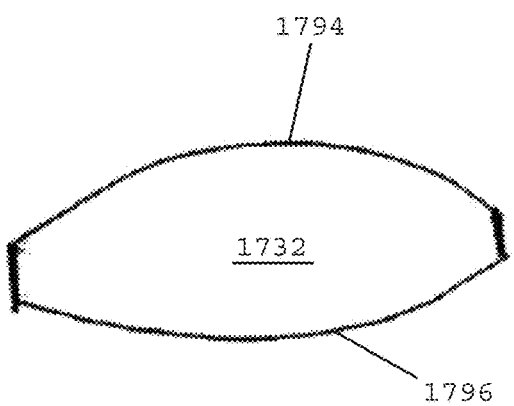
FIG. 17 shows a top plan view of a plate for a tissue anchor for joining tissue layers, in accordance with one embodiment of the present patent application.

Referring to FIG. 17, in one embodiment, a plate 1732 for a tissue anchor may have a first convexly curved edge 1794 and second convexly curved edge 1796 that faces away from the first convexly curved edge 1694.

Figure 18:
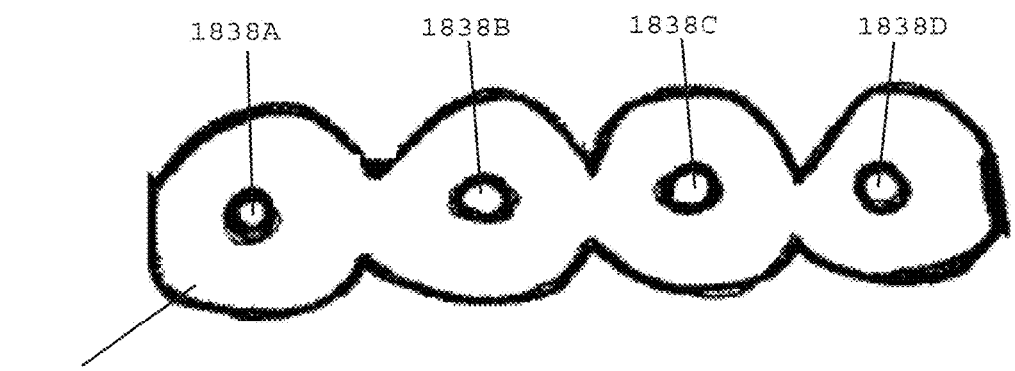
FIG. 18 shows a top plan view of a plate for a tissue anchor for joining tissue layers, in accordance with one embodiment of the present patent application.

Referring to FIG. 18, in one embodiment, a plate 1832 for a tissue anchor disclosed herein may include a plurality of apertures 1838A-1838D that are spaced from one another along the length of the plate 1832.

Figure 19:
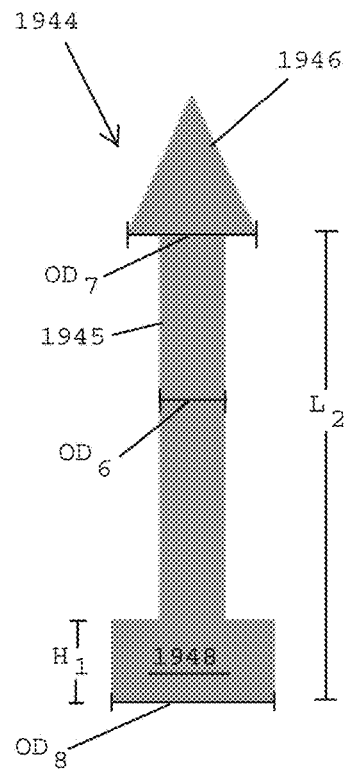
FIG. 19 shows a front elevational view of a barbed pin for a tissue anchor for joining tissue layers, in accordance with one embodiment of the present patent application.

Referring to FIG. 19, in one embodiment, an elongated pin 1944 adapted to slide through an aperture of a plate (e.g., the second pins 144A-144C shown in FIG. 1A-1) preferably includes an elongated shaft 1945 having an outer diameter $OD_6$ of about 0.5-5 mm and a length $L_2$ of about 2-15 mm. The elongated shaft 1945 preferably has an upper end having a tissue engaging barb 1946 secured thereto. The tissue engaging barb 1996 desirably has a base defining an outer diameter $OD_7$ of about 0.7-5 mm. In one embodiment, the elongated shaft 1945 has a lower end including a stop 1948 secured thereto. In one embodiment, the stop 1948 has an outer diameter $OD_8$ of about 0.7-5 mm and a height $H_1$ of about 0.2-2 mm.

Figure 20:
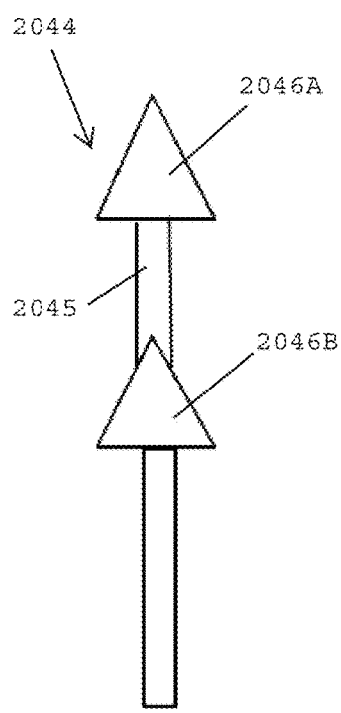
FIG. 20 shows a front elevational view of an elongated pin for a tissue anchor for joining tissue layers, the elongated pin having two barbs, in accordance with one embodiment of the present patent application.

Referring to FIG. 20, in one embodiment, an elongated pin 2044 for a tissue anchor disclosed herein preferably has an elongated shaft 2045 with a first tissue engaging barb 2046A attached to an upper end of the elongated shaft 2045 and a second tissue engaging barb 2046B attached to a mid-section of the elongated shaft 2045.

Figure 21:
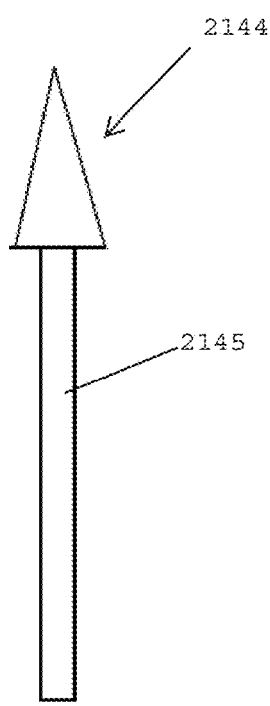
FIG. 21 shows a front elevational view of an elongated pin for a tissue anchor for joining tissue layers, the elongated pin having an elongated barb, in accordance with one embodiment of the present patent application.

Referring to FIG. 21, in one embodiment, an elongated pin 2144 for a tissue anchor preferably includes an elongated shaft 2145 having an upper end with a tissue engaging barb 2146 attached thereto. The tissue engaging barb 2146 is elongated relative to other embodiments shown herein (e.g., the elongated pin shown in FIG. 19) and preferably has a barb length that is greater than the barb shown in FIG. 19 and a barb width that is smaller than the barb shown in FIG. 19.

Figure 22:
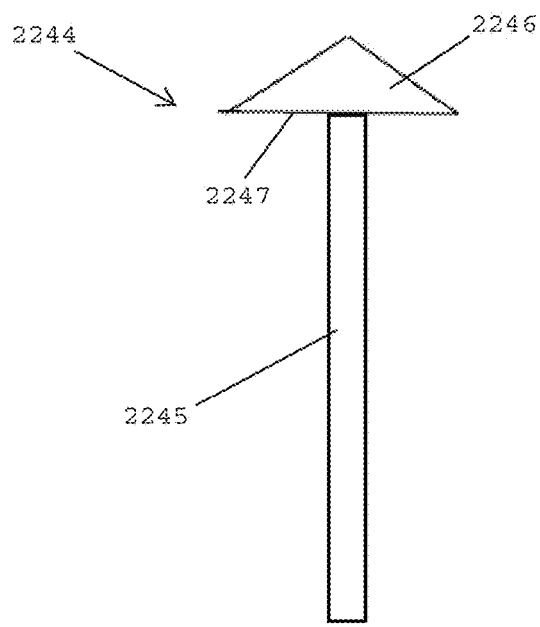
FIG. 22 shows a front elevational view of an elongated pin for a tissue anchor for joining tissue layers, the elongated pin having a barb with a widened base, in accordance with one embodiment of the present patent application.

Referring to FIG. 22, in one embodiment, a pin 2244 for a tissue anchor disclosed herein preferably has an elongated shaft 2245 with an upper end including a tissue engaging barb 2246. The tissue engaging barb 2246 has a base 2247 that is wider relative to other embodiments shown herein (e.g., the elongated pin shown in FIG. 19) and preferably has a barb length that is less than the barb shown in FIG. 19 and a barb width that is greater than the barb shown in FIG. 19.

Figure 23:
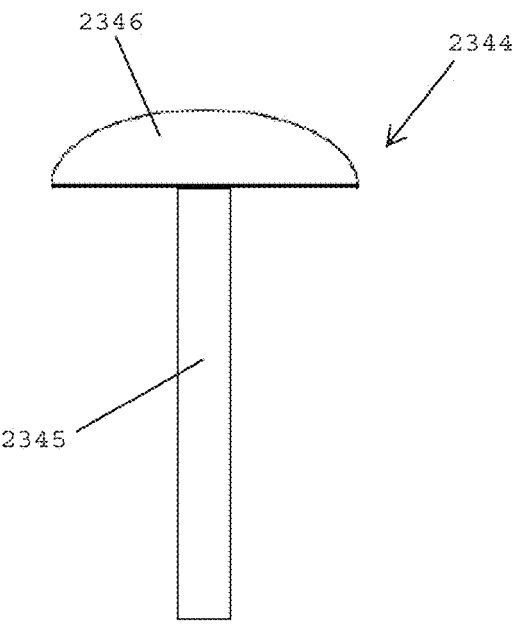
FIG. 23 shows a front elevational view of an elongated pin for a tissue anchor for joining tissue layers, the elongated pin having a mushroom-shaped barb at a distal end thereof, in accordance with one embodiment of the present patent application.

Referring to FIG. 23, in one embodiment, a pin 2344 for tissue anchor preferably includes an elongated shaft 2345 having an upper end with a mushroom-shaped barb 2346 attached thereto.

Figure 24:
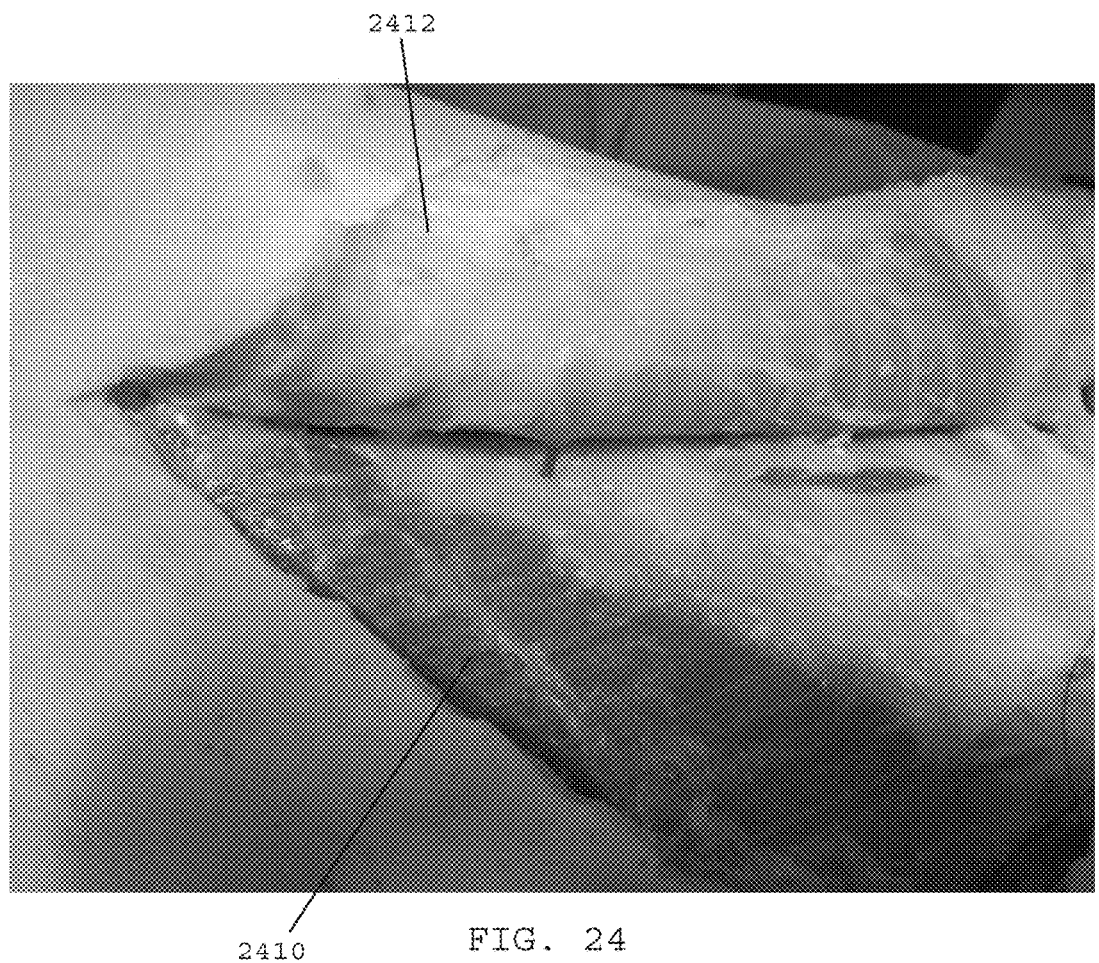
FIG. 24 shows two tissue layers prior to the layers being joined together using a plurality of tissue anchors, in accordance with one embodiment of the present patent application.

Referring to FIG. 24, in one embodiment, one or more of the tissue anchors disclosed herein may be used for re-joining a first tissue layer 2410 and a second tissue layer 2412 that have been separated from one another during a surgical procedure. In one embodiment, one or more tissue anchors are placed atop the exposed surface of the first tissue layer 2410. The tissue anchors may be arranged in an area array overlying the first tissue layer. In one embodiment, one tissue anchors may be positioned in a first area of the first tissue layer and fewer tissue anchors may be positioned in a second area of the first tissue layer. For example, fewer tissue anchors may be positioned adjacent to the area where the flap of second tissue layer joins the first tissue later, and more tissue anchors may be positioned at the outer perimeter of the second tissue layer. After the tissue anchors have been positioned atop the first tissue layer 2410, the second tissue layer is moved to cover the positioned tissue anchors and the first tissue layer, and the second tissue layer is compressed onto the tissue anchors and the first tissue layer so that the first and second pins of the tissue anchors will advance into the first and second tissue layers for holding the tissue layers together for healing.

Figure 25:
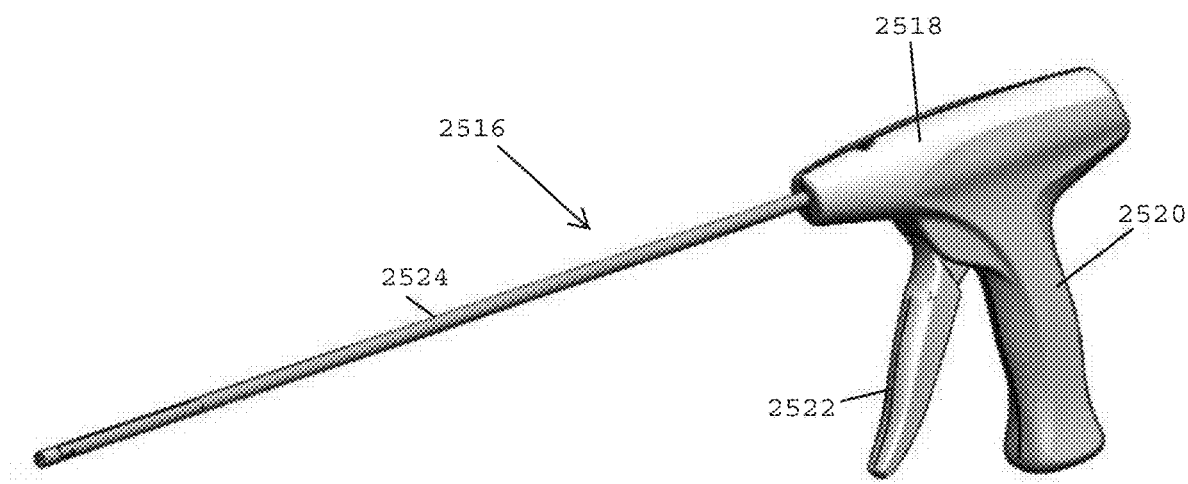
FIG. 25 shows a perspective view of an applicator instrument used to deploy tissue anchors for joining tissue layers, in accordance with one embodiment of the present patent application.

Referring to FIG. 25, in one embodiment, an applicator instrument 2516 for dispensing tissue anchors preferably includes a housing 2518, a handle 2520, a trigger 2522, and an elongated cannula 2524 extending from the housing. In one embodiment, a plurality of tissue anchors are pre-positioned inside the applicator instrument 2516 and a single tissue anchor is dispensed each time the trigger 2522 is squeezed. In one embodiment, a cartridge containing a plurality of tissue anchors may be securable to the applicator instrument for providing a supply of tissue anchors.

The tissue anchors disclosed herein may be made of conventional, biocompatible, absorbable materials, non-absorbable materials, and combinations of absorbable and non-absorbable materials. Preferred non-absorbable materials include polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof. Preferred absorbable polymeric materials include polydioxanone, polyglactin, polyglycolic acid, copolymers of glycolide and lactide, polyoxaesters, and poliglecaprone. In addition, metals or ceramics may be suitable for certain applications, such as instances where specific strength or corrosion resistance is necessary. In one preferred embodiment, the tissue anchors may preferably include a polymer blend of polyvinylidene fluoride and polyvinylidene fluoride-co-hexafluoropropylene material. In addition, any of these materials may have conventional surface modifications that include coatings, plasma treatments, therapeutics, and the like.

In one embodiment, the tissue anchors disclosed herein may be coated with an antimicrobial agent, such as triclosan, for reducing and minimizing the risk of bacterial colonization, infection and complications. In one embodiment, any one of the components of the tissue anchors disclosed herein, such as a plate, one or more of the elongated pins, and/or one or more of the barbs may be coated with an antimicrobial agent.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of joining together two layers of tissue comprising:
   positioning a tissue anchor over a first tissue layer, said tissue anchor including a plate having top and bottom surfaces, an array of first pins projecting from said bottom surface of said plate that oppose said first tissue layer, and an array of second pins projecting from said top surface of said plate that face away from said first tissue layer;
   after the positioning step, placing a second tissue layer over said first tissue layer and said tissue anchor so that said array of second pins oppose said second tissue layer, wherein said tissue anchor is positioned between said first and second tissue layers;
   after the placing step, pressing said second tissue layer onto said tissue anchor and toward said first tissue layer so that said first pins advance into said first tissue layer and said second pins advance into said second tissue layer for joining together said first and second tissue layers.

2. The method as claimed in claim 1, further comprising positioning a plurality of said tissue anchors between said first and second tissue layers, wherein during the pressing step said first pins of said respective tissue anchors advance into said first tissue layer and said second pins of said respective tissue anchors advance into said second tissue layer for joining together said first and second tissue layers.

3. The method as claimed in claim 1, wherein each said first pin includes an elongated shaft having a lower end with a first barb located below said bottom surface of said plate for retaining said first pin in said first tissue layer, and wherein each said second pin includes an elongated shaft having an upper end with a second barb located above said top surface of said plate for retaining said second pin in said second tissue layer.

4. The method as claimed in claim 3, further comprising:
   said plate including an array of second pin apertures that are offset from said first pins, wherein each said second pin aperture has a diameter, and wherein each said second pin aperture extends from said top surface to said bottom surface of said plate; and
   said array of second pins extending through said second pin apertures, wherein each said second pin comprises said elongated shaft having said upper end including said second barb located above said top surface of said plate and a lower end including a stop that is located below said bottom surface of said plate.

5. The method as claimed in claim 4, wherein said elongated shafts of said second pins have outer diameters that are smaller than said diameters of said second pin apertures for enabling said second pins to slide freely within said second pin apertures of said plate.

6. The method as claimed in claim 5, wherein said second pins are free to move independently of one another when sliding within said respective second pin apertures of said plate.

7. The method as claimed in claim 5, wherein said second pins are configured to slide along axes that are perpendicular to said top and bottom surfaces of said plate.

8. The method as claimed in claim 5, wherein said second barbs and said stops of said second pins have outer diameters that are larger than said diameters of said respective second pin apertures of said plate.

9. The method as claimed in claim 5, wherein at least one of said second pins comprises a locking element that is located between said upper and lower ends of said elongated shaft of said second pin, and wherein said locking element projects outwardly from said elongated shaft and is adapted to engage said plate for allowing said upper end of said elongated shaft and said second barb to move a predetermined distance away from said top surface of said plate while preventing said upper end of said elongated shaft and said second barb from reversing direction and moving back toward said top surface of said plate after said upper end of said elongated shaft and said second barb have moved the predetermined distance away from said top surface of said plate.

10. The method as claimed in claim 1, wherein said second pins are offset from and not in axial alignment with said first pins of said tissue anchor.

11. The method as claimed in claim 1, wherein said first and second pins extend along respective axes that are parallel to one another.

12. A method of joining together two parallel tissue layers comprising:
   positioning a tissue anchor between first and second tissue layers, said tissue anchor including a plate having top and bottom major surfaces, an array of first pins fixed to and projecting away from said bottom major surface of said plate that are in contact with said first tissue layer, and an array of second pins projecting away from said top major surface of said plate that are in contact with said second tissue layer, wherein said plate has second pin apertures that are offset from said first pins, and wherein said second pins are configured to slide within said respective second pin apertures;

pressing said second tissue layer onto said tissue anchor and toward said first tissue layer so that said first pins advance into said first tissue layer and said second pins advance into said second tissue layer for joining together said first and second parallel tissue layers.

13. The method as claimed in claim 12, further comprising positioning a plurality of said tissue anchors between said first and second tissue layers, wherein during the pressing step said first pins of said respective tissue anchors advance into said first tissue layer and said second pins of said respective tissue anchors advance into said second tissue layer for joining together said first and second tissue layers.

14. The method as claimed in claim 13, wherein each said first pin includes an elongated shaft having a lower end with a first barb located below said bottom major surface of said plate for retaining said first pin in said first tissue layer, and wherein each said second pin includes an elongated shaft having an upper end with a second barb located above said top major surface of said plate for retaining said second pin in said second tissue layer and a lower end including a stop that is located below said bottom major surface of said plate.

15. The method as claimed in claim 14, wherein each said second pin aperture has a diameter, and wherein each said second pin aperture extends from said top surface to said bottom surface of said plate.

16. The method as claimed in claim 15, wherein said elongated shafts of said second pins have outer diameters that are smaller than said diameters of said respective second pin apertures for allowing said elongated shafts of said second pins to slide independently of one another within said respective second pin apertures.

17. A method of joining together two tissue layers comprising:

obtaining a tissue anchor including a plate having top and bottom surfaces, an array of first pins projecting from said bottom surface of said plate, and an array of second pins projecting from said top surface of said plate;

positioning said tissue anchor between first and second tissue layers so that said first pins are in contact with said first tissue layer and said second pins are in contact with said second tissue layer;

pressing said second tissue layer onto said tissue anchor and toward said first tissue layer so that said first pins advance into said first tissue layer and said second pins advance into said second tissue layer for joining together said first and second tissue layers.

18. The method as claimed in claim 17, wherein said plate comprises an array of second pin apertures that are offset from said first pins, wherein said array of second pins extend through said second pin apertures so that said second pins are offset from and not in axial alignment with said first pins, and wherein said second pins are free to slide independently of one another through said respective second pin apertures of said plate.

19. The method as claimed in claim 18, wherein each said first pin includes an elongated shaft having an upper end fixed to said plate and a lower end with a first barb facing away from said bottom surface of said plate, and wherein each said second pin has an elongated shaft having an upper end including a second barb located above said top surface of said plate and a lower end including a stop that is located below said bottom surface of said plate, wherein said elongated shafts of said second pins have outer diameters that are smaller than diameters of said second pin apertures for allowing said elongated shafts of said second pins to slide within said second pin apertures, and wherein said second barbs and said stops of said second pins have outer diameters that are larger than said diameters of said second pin apertures.

20. The method as claimed in claim 17, further comprising positioning a plurality of said tissue anchors between said first and second tissue layers, wherein during the pressing step said first pins of said respective tissue anchors advance into said first tissue layer and said second pins of said respective tissue anchors advance into said second tissue layer for joining together said first and second tissue layers.

* * * * *